US012409190B2

(12) United States Patent
Reif et al.

(10) Patent No.: US 12,409,190 B2
(45) Date of Patent: Sep. 9, 2025

(54) MILK DERIVED EXTRACELLULAR VESICLES FOR USE IN TREATING INFLAMMATORY BOWEL DISEASE

(71) Applicant: HADASIT MEDICAL RESEARCH SERVICES & DEVELOPMENT LTD., Jerusalem (IL)

(72) Inventors: Shimon Reif, Jerusalem (IL); Regina Golan-Gerstl, Maale Michmash (IL)

(73) Assignee: HADASIT MEDICAL RESEARCH SERVICES & DEVELOPMENT LTD., Jerusalem (IL)

( * ) Notice: Subject to any disclaimer, the term of this patent is extended or adjusted under 35 U.S.C. 154(b) by 784 days.

(21) Appl. No.: 17/595,045

(22) PCT Filed: May 13, 2020

(86) PCT No.: PCT/IL2020/050518
§ 371 (c)(1),
(2) Date: Nov. 7, 2021

(87) PCT Pub. No.: WO2020/230129
PCT Pub. Date: Nov. 19, 2020

(65) Prior Publication Data
US 2022/0202866 A1 Jun. 30, 2022

Related U.S. Application Data

(60) Provisional application No. 62/847,339, filed on May 14, 2019.

(51) Int. Cl.
A61K 36/00 (2006.01)
A61K 9/00 (2006.01)
A61K 9/127 (2006.01)
A61K 31/7105 (2006.01)
A61K 35/20 (2006.01)
A61K 38/18 (2006.01)
A61P 1/12 (2006.01)

(52) U.S. Cl.
CPC ............ A61K 35/20 (2013.01); A61K 9/0053 (2013.01); A61K 9/127 (2013.01); A61K 31/7105 (2013.01); A61K 38/1841 (2013.01); A61P 1/12 (2018.01)

(58) Field of Classification Search
None
See application file for complete search history.

(56) References Cited

U.S. PATENT DOCUMENTS

| | | | | |
|---|---|---|---|---|
| 10,874,114 B2 * | 12/2020 | Reif | ..................... | A61K 9/1276 |
| 2004/0097714 A1 | 5/2004 | Maubois et al. | | |
| 2014/0302205 A1 | 10/2014 | Melnik | | |
| 2016/0000710 A1 | 1/2016 | Gupta et al. | | |
| 2018/0343882 A1 | 12/2018 | Reif et al. | | |

FOREIGN PATENT DOCUMENTS

| | | | | |
|---|---|---|---|---|
| CN | 101874108 A | 10/2010 | | |
| CN | 105412153 A | 3/2016 | | |
| EP | 1 800 675 A1 | 6/2007 | | |
| EP | 2455486 A1 | 5/2012 | | |
| EP | 2896294 A1 | 7/2015 | | |
| EP | 3192518 A1 * | 7/2017 | ............ | A61K 35/20 |
| FR | 2 827 290 A1 | 1/2003 | | |
| WO | WO 2013/023982 A1 | 8/2012 | | |
| WO | WO 2014/036726 A1 | 3/2014 | | |
| WO | WO 2014/134132 A1 | 9/2014 | | |
| WO | WO-2017090049 A1 * | 6/2017 | ........... | A23C 9/1512 |
| WO | 2018/102397 A1 | 6/2018 | | |
| WO | WO-2018170332 A1 * | 9/2018 | ............ | A61K 35/20 |
| WO | WO-2019236873 A1 * | 12/2019 | ............ | A23L 33/40 |

OTHER PUBLICATIONS

Axelrad et al. (2016) World J. Gastroenterol. 22(20): 4794-4801. (Year: 2016).*
Casella et al. (2010) J. Crohn's and Colitis 4, 384-389. (Year: 2010).*
Danese et al. (2005) World J. Gastroenterol. 11(46): 7227-7236. (Year: 2005).*
Pieters et al. (2015) PLoS ONE 10(3): 14 pages (Year: 2015).*
Veloso (2004) Aliment. Pharmacol. Ther. 20(Suppl. 4): 50-53. (Year: 2004).*
Chen et al., "Decreased miRNA-148a is associated with lymph node metastasis and poor clinical outcomes and functions as a suppressor of tumor metastasis in non-small cell lung cancer," Oncology Reports, 30: 1832-1840 (2013).
Melnik et al., "Milk: an exosomal microRNA transmitter promoting thymic regulatory T cell maturation preventing the development of atopy?," Journal of Translational Medicine, 12:43 (2014).
Admyre et al., (2007) Exosomes with immune modulatory features are present in human breast milk. J Immunol 179 (3): 1969-1978.
Alsaweed et al., (2015) MicroRNAs in Breastmilk and the Lactating Breast: Potential Immunoprotectors and Developmental Regulators for the Infant and the Mother. Int J Environ Res Public Health 12(11): 13981-14020.
Arntz et al., (2015) Oral administration of bovine milk derived extracellular vesicles attenuates arthritis in two mouse models. Mol Nutr Food Res 59(9): 1701-1712.
Benmoussa et al., "Concentrates of two subsets of extracellular vesicles from cow's milk modulate symptoms and inflammation in experimental colitis," Scientific Reports, 9:14661 (2019).
Bernstein et al., (2001) Cancer risk in patients with inflammatory bowel disease: a population-based study. Cancer 91(4): 854-862.

(Continued)

Primary Examiner — Russell G Fiebig
(74) Attorney, Agent, or Firm — Allan A. Fanucci

(57) ABSTRACT

The present invention is directed to compositions containing exosomes isolated from milk and methods and uses thereof for treating inflammatory bowel disease (IBD) and conditions related thereto. In particular, disclosed are exosomes derived from milk and enteral formulations supplemented therewith for use in treating IBD. The compositions are preferably formulated for rectal administration and the exosomes comprise one or more miRNA molecules and TGF-β.

18 Claims, 13 Drawing Sheets
Specification includes a Sequence Listing.

(56) References Cited

OTHER PUBLICATIONS

Chen et al., (2016) Porcine milk-derived exosomes promote proliferation of intestinal epithelial cells. Sci Rep 6: 33862; 12 pages.
El Andaloussi et al., (2013) Extracellular vesicles: biology and emerging therapeutic opportunities. Nat Rev Drug Discov 12(5): 347-357.
Golan-Gerstl et al., (2016) Expression and biological function of miRNA in breast milk. 10th Congress of the International Society of Nutrigenetics/Nutrigenomics (ISNN). May 22-26, 2016, Tel Aviv, Israel. J Nutrigenet Nutrigenomics 9: 151-210; p. 164. Abstract.
Golan-Gerstl et al., (2017) Characterization and biological function of milk-derived miRNAs. Mol Nutr Food Res 61(10): 1700009; 11 pages.
Hartnett and Egan (2012) Inflammation, DNA methylation and colitis-associated cancer. Carcinogenesis 33(4): 723-731.
Kanwar et al., (2016) Comparative activities of milk components in reversing chronic colitis. J Dairy Sci 99(4): 2488-2501.
Mao et al., (2017) Exosomes Derived from Human Umbilical Cord Mesenchymal Stem Cells Relieve Inflammatory Bowel Disease in Mice. Biomed Res Int 2017: 5356760; 13 pages.
Pieters et al., (2015) Commercial cow milk contains physically stable extracellular vesicles expressing immunoregulatory TGF-β. PLoS One 10(3): e0121123; 14 pages.
Verhasselt et al., (2008) Breast milk-mediated transfer of an antigen induces tolerance and protection from allergic asthma. Nat Med 14(2): 170-175.
Wang et al., (2017) Exosomes Derived from Dendritic Cells Treated with Schistosoma japonicum Soluble Egg Antigen Attenuate DSS-Induced Colitis. Front Pharmacol 8: 651; 10 pages.
Wolf et al., (2015) The Intestinal Transport of Bovine Milk Exosomes Is Mediated by Endocytosis in Human Colon Carcinoma Caco-2 Cells and Rat Small Intestinal IEC-6 Cells. J Nutr 145(10): 2201-2206.
Yang et al., (2015) Extracellular Vesicles Derived from Bone Marrow Mesenchymal Stem Cells Protect against Experimental Colitis via Attenuating Colon Inflammation, Oxidative Stress and Apoptosis. PLoS One 10(10): e0140551; 19 pages.
Zhou et al., (2012) Immune-related microRNAs are abundant in breast milk exosomes. Int J Biol Sci 8(1): 118-123.
International Application No. PCT/IL2020/050518, International Search Report, mailed Aug. 18, 2020.
International Application No. PCT/IL2020/050518, Written Opinion of the International Searching Authority, mailed Aug. 18, 2020.
Li et al., "Bovine milk-derived exosomes enhance goblet cell activity and prevent the development of experimental necrotizing enterocolitis," PLoS ONE 14(1): e0211431 (2019).
Ordas et al., "Anti-TNF Monoclonal Antibodies in Inflammatory Bowel Disease: Pharmacokinetics-Based Dosing Paradigms," Clinical Pharmacology & Therapeutics, 91(4): 635-646 (2012).
Huguet et al., "Systematic Review With Meta-Analysis: Anti-TNF Therapy in Refractory Pouchitis and Crohn's Disease—Like Complications of the Pouch After Ileal Pouch-Anal Anastomosis Following Colectomy for Ulcerative Colitis," Inflamm Bowel Dis., 24(2): 261-268 (2018).
Akane Hasegawa, 2011, vol. 49, No. 6, pp. 392-397.
Hibi et al, 2001, vol. 22, No. 2, pp. 115-121.

\* cited by examiner

FIG. 1A
| SOURCE OF EXOSOMES | NUMBER |
|---|---|
| COW (Protocol B) | $4.78 \times 10^8$ |
| HUMAN (Protocol B) | $2.33 \times 10^8$ |
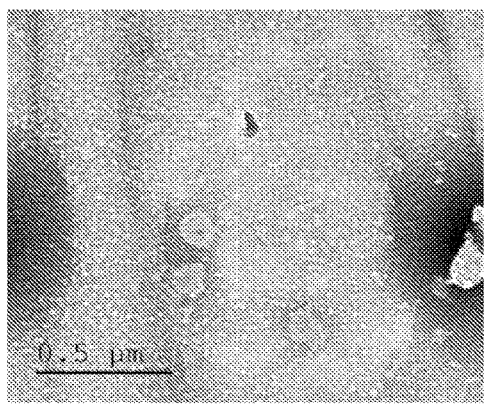
FIG. 1B
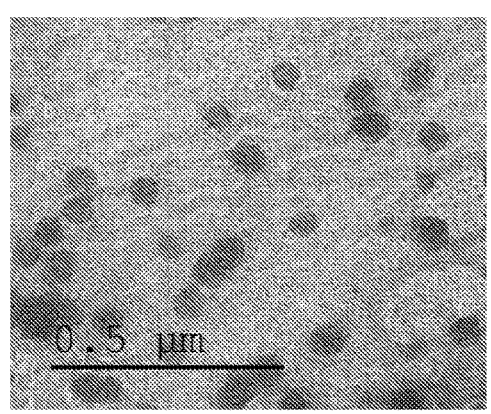
FIG. 1C
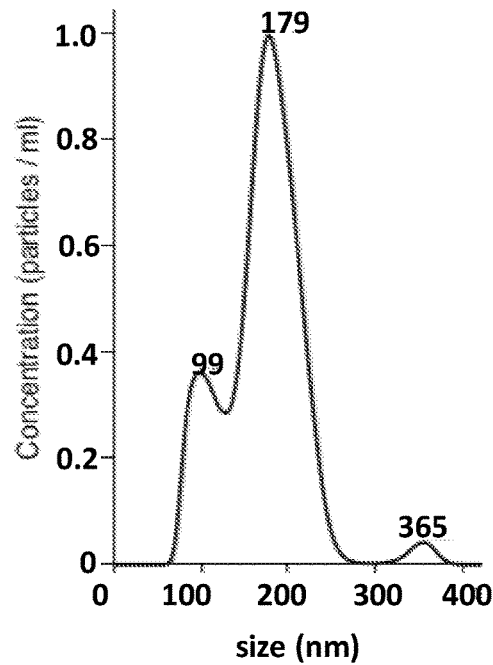
FIG. 1D
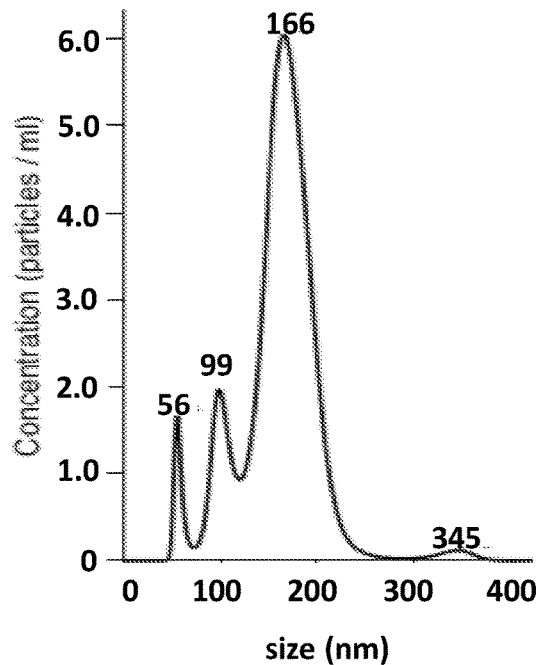
FIG. 1E FIG. 1F
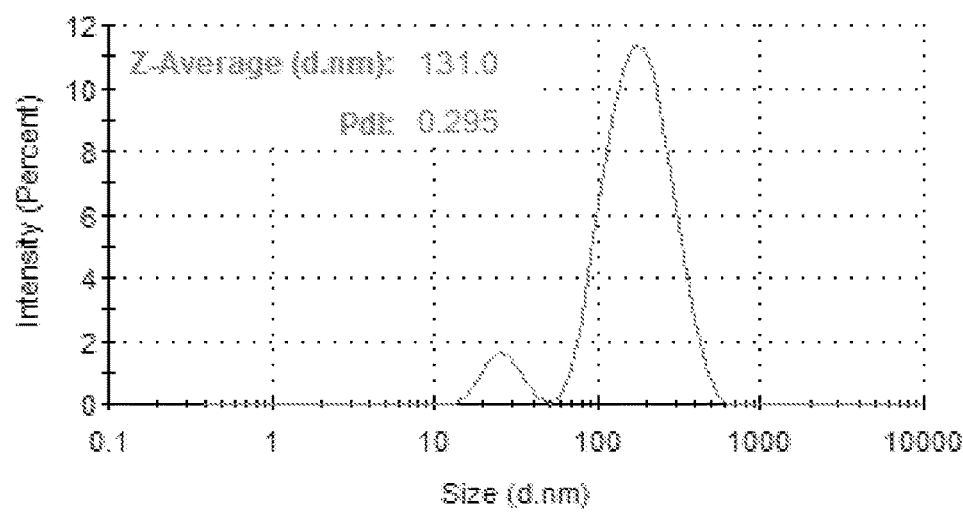
FIG. 1G
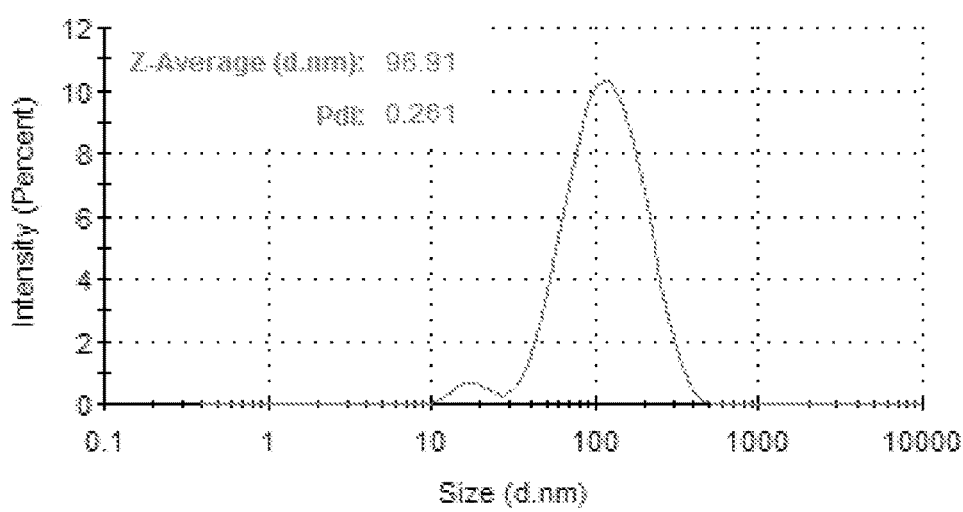
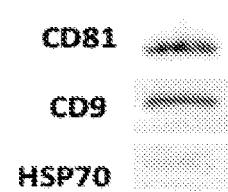
FIG. 1H          FIG. 1I

CONTROL

DSS

EXO (-)

CONTROL

DSS

EXO (+)

```
                         SEQUENCE LISTING

<160> NUMBER OF SEQ ID NOS: 8

<210> SEQ ID NO 1
   <211> LENGTH: 24
   <212> TYPE: DNA
   <213> ORGANISM: Artificial Sequence
   <220> FEATURE:
   <223> OTHER INFORMATION: synthetic oligonucleotide

<400> SEQUENCE: 1
cgctcagtgc actacagaac tttt                                           24

<210> SEQ ID NO 2
   <211> LENGTH: 20
   <212> TYPE: DNA
   <213> ORGANISM: Artificial Sequence
   <220> FEATURE:
   <223> OTHER INFORMATION: synthetic oligonucleotide

<400> SEQUENCE: 2
gcaaattcgt gaagcgttcc                                                20

<210> SEQ ID NO 3
   <211> LENGTH: 20
   <212> TYPE: DNA
   <213> ORGANISM: Artificial Sequence
   <220> FEATURE:
   <223> OTHER INFORMATION: synthetic oligonucleotide

<400> SEQUENCE: 3
gttctgtccc tttcactcac                                                20

<210> SEQ ID NO 4
   <211> LENGTH: 18
   <212> TYPE: DNA
   <213> ORGANISM: Artificial Sequence
   <220> FEATURE:
   <223> OTHER INFORMATION: synthetic oligonucleotide

<400> SEQUENCE: 4
tgcctcttct gccagttc                                                  18

<210> SEQ ID NO 5
   <211> LENGTH: 25
   <212> TYPE: DNA
   <213> ORGANISM: Artificial Sequence
   <220> FEATURE:
   <223> OTHER INFORMATION: synthetic oligonucleotide

<400> SEQUENCE: 5
gagtcacaga aggagtggct aagga                                          25

<210> SEQ ID NO 6
   <211> LENGTH: 25
   <212> TYPE: DNA
   <213> ORGANISM: Artificial Sequence
   <220> FEATURE:
```

```
<223> OTHER INFORMATION: synthetic oligonucleotide

<400> SEQUENCE: 6
cgcactaggt ttgccgagta gatct                                        25

<210> SEQ ID NO 7
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 7
gccttccgtg ttcctacc                                                18

<210> SEQ ID NO 8
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 8
cttcaccacc ttcttgatgt c                                            21
```

MILK DERIVED EXTRACELLULAR VESICLES FOR USE IN TREATING INFLAMMATORY BOWEL DISEASE

This application is a 371 filing of International Patent Application PCT/IL2020/050518 filed May 13, 2020, which claims the benefit of U.S. provisional application No. 62/847,339 filed May 14, 2019.

FIELD OF THE INVENTION

The present invention relates to milk derived exosomes for treating inflammatory bowel disease (IBD). Particularly, the present invention relates to compositions comprising exosomes isolated from milk for use in treating IBD or a condition associated therewith, wherein the compositions are formulated for enteral administration.

BACKGROUND OF THE INVENTION

Exosomes are nanovesicles with a diameter from about 30 to 150 nm which are capable of packing various constituents, including proteins, lipids, mRNAs, and miRNAs. Exosomes can transfer their cargo to recipient cells, and as such serve as extracellular messengers which can mediate cell-cell communication. Exosomes have been implicated as potential new treatment modality of autoimmune and inflammatory diseases such as rheumatoid arthritis.

Exosomes are found in physiological fluids, such as in serum, bronchoalveolar lavage, urine, and in breast milk. Exosomes derived from mammalian milk were found to have the ability to transfer biological macromolecules, e.g., miRNAs, intracellularly by fusion. It was shown that mammalian milk contains a high concentration of exosomes carrying beneficial miRNAs, such as miRNA-148, which can be taken up by intestinal epithelial cells (Golan-Gerstl R, et. al., (2017), Characterization and biological function of milk-derived miRNAs. Mol Nutr Food Res. 2017; 61(10)). Mammalian milk was also shown to contain exosomes carrying immune-suppressive cytokine, such as TGF-$\beta$ (Pieters B C H, et al. (2015). Commercial cow milk contains physically stable extracellular vesicles expressing immunoregulatory TGF-$\beta$ (PLOS ONE, DOI:10.1371/journal.pone.0121123). Further studies have shown that oral delivery of vesicles isolated from cow milk can ameliorate experimental arthritis (Arntz O J, et al. (2015), Oral administration of bovine milk derived extracellular vesicles attenuates arthritis in two mouse models. Mol Nutr Food Res., 59:1701-12).

Colitis is an inflammatory condition of the inner lining of the colon. There are various causes of colitis, including infection, inflammatory bowel disease (IBD), loss of blood supply in the colon, or invasion of the colon wall with collagen or with lymphocytes. There are various types of colitis, including ulcerative colitis (UC), Crohn's colitis, ischemic colitis, collagenous colitis, lymphocytic colitis, and microscopic colitis.

Inflammatory bowel disease (IBD) is a chronic relapsing inflammatory disease of the gastrointestinal tract that is traditionally characterized by two major phenotypes: Crohn's disease (CD) and ulcerative colitis (UC). Both of these phenotypes are usually characterized by severe occasionally bloody diarrhea, abdominal pain, fatigue, and weight loss. Ulcerative colitis is limited to the colon whereas Crohn's disease can occur anywhere between the mouth and the anus. In Crohn's disease there are healthy parts of the intestine which are separated by inflamed areas (skipped areas). Ulcerative colitis, on the other hand, is a continuous inflammation of the colon which does not involve the small intestine. Ulcerative colitis is a superficial inflammation which affects the mucosal layer of the colon, whereas in Crohn's disease the inflammation is transmural and can affect all intestine layers.

Current therapies for IBD treatment mainly focus on immunosuppression drugs. However, patients with IBD frequently experience relapses, even with current medical therapies. It is well established that a significant part of patients does not respond adequately to current treatments. Further, patients with IBD are known to have an increased risk of colorectal cancer (CRC). IBD patients can develop dysplastic lesion, the dysplastic precursor of which is usually adenomatous polyps.

Wang L, et al (Front Pharmacol. 2017, 8:651) disclose that exosomes derived from dendritic cells which were treated with *Schistosoma japonicum* soluble egg antigen were capable of attenuating dextran sulfate sodium (DSS)-induced colitis when injected intraperitoneally to the mice.

Mao F, et. al. (Biomed Res Int. 2017; 2017:5356760) disclose that exosomes derived from human umbilical cord mesenchymal stem cells relieved DSS-induced IBD in mice when injected intravenously.

WO 2017/090049 to the present inventors discloses microvesicles isolated from milk, compositions comprising same and uses thereof for the preparation of milk formulas. According to WO 2017/090049, the microvesicles which include exosomes and fat globules encapsulate various miRNA molecules.

There remains an unmet need for improved compositions and methods for treatment and prevention of IBD or conditions associated thereof.

SUMMARY OF THE INVENTION

The present invention provides compositions comprising exosomes obtained from milk for use in treating inflammatory bowel disease (IBD) or conditions associated therewith, wherein the exosomes comprise one or more miRNA molecules and TGF-$\beta$, and wherein the compositions are formulated for enteral administration. The present invention further provides compositions comprising exosomes obtained from milk, wherein the exosomes comprise one or more miRNA molecules and TGF-$\beta$, and wherein the compositions are formulated for rectal administration. The present invention further provides methods for treating IBD or conditions associated therewith comprising administering to a subject in need of such treatment an enteral composition comprising said exosomes.

The present invention stems, in part, from the surprising finding that exosomes obtained or derived from milk contain high amounts of the known anti-inflammatory cytokine TGF-$\beta$, specifically TGF-$\beta$1.

It is disclosed for the first time that exosomes isolated from the skim fraction of human or cow's milk or from the fat fraction of human or cow's milk, when administered orally to an animal model of colitis, i.e., dextran-sulfate sodium (DSS)-induced colitis in mice, were highly effective in reducing or alleviating characteristic symptoms of the disease in these mice. It is now disclosed that milk derived exosomes when administered orally not only were effective in preventing the weight loss of the colitic mice, but also reduced the inflammation in their colon and attenuated the severity of colitis.

The present invention further discloses the unexpected findings that the milk derived exosomes administered orally to DSS-induced colitic mice increased the expression of TGF-β1 protein and of few miRNA molecules, including let7a, miR-320, miR-375, and miR-148a, as well as reduced the expression of proinflammatory cytokines, e.g., TNF-α and IL-6, in the colon of these mice.

It is now further disclosed that the milk derived exosomes administered orally were effective not only in treating colitis in the DSS-treated mice both also in attenuating the development of the disease. Also, the effect of milk derived exosomes on reducing the severity of colitis in mice was greater than, or even superior to, the effect of a known nutritionally powdered feed, i.e., Modulen® IBD. Without being bound to any theory or mechanism of action, the improved therapeutic effect of the milk derived exosomes on colitis may be due to an increased stability of TGF-β, particularly TGF-β1, contained or encapsulated within the exosomes as compared to its free, non-encapsulated form. Such improved therapeutic effect may also be due to the presence of TGF-β1, rather than TGF-β2, as a major form of TGF-β contained in the milk derived exosomes.

Thus, the enteral compositions comprising milk derived exosomes of the present invention are safe, provide a highly effective preventive and/or therapeutic medication of IBD conditions, are more efficacious than a dietary formulation currently available for IBD patients, and are clearly more patient compliant than parenteral formulations.

According to a first aspect, the present invention provides a composition comprising exosomes obtained from milk for use in treating inflammatory bowel disease (IBD) or a condition associated therewith, wherein the exosomes comprise one or more miRNA molecules and TGF-β, and wherein the composition is formulated for enteral administration.

According to some embodiments, the milk is bovine, goat, or human milk. According to additional embodiments, the exosomes being obtained from a skim fraction of the milk and/or from a fat fraction of the milk. According to further embodiments, the milk is obtained before, during and/or after lactation. According to still further embodiments, the milk is pasteurized or not pasteurized. Each possibility represents a separate embodiment of the invention.

According to further embodiments, the one or more miRNA molecules are selected from the group consisting of let-7a, miR-320, miR-375, and miR-148a. Each possibility represents a separate embodiment of the invention. According to yet further embodiments, the miRNA molecules comprise let-7a, miR-320, miR-375, and miR-148a.

According to further embodiment, the TGF-β is TGF-β1.

According to additional embodiments, the exosomes further comprise at least one biologically active compound selected from the group consisting of proteins, peptides, nucleic acid molecules, and lipids.

According to further embodiments, the exosomes comprise less than about 20% (w/w) casein of the total protein of the exosomes.

According to some embodiments, the inflammatory bowel disease (IBD) is selected from the group consisting of Crohn's disease and ulcerative colitis. Each possibility represents a separate embodiment of the invention.

According to additional embodiments, ulcerative colitis is distal colitis.

According to further embodiments, distal colitis is selected from the group consisting of proctitis, proctosigmoiditis, and left-sided colitis. Each possibility represents a separate embodiment of the invention.

According to one embodiment, the condition associated with IBD is pouchitis.

According to some embodiments, the composition is formulated for oral administration or for tube feeding.

According to further embodiments, the composition is formulated for rectal administration.

According to yet further embodiments, the composition is formulated as a nutraceutical or pharmaceutical composition, a dietary formulation, or a dietary supplement.

According to still further embodiments, the composition formulated for rectal administration is present in a form of an enema, suppository, or foam.

According to some embodiments, the exosomes are present in the composition in a therapeutically effective amount ranging from about 0.1 mg to about 250 mg/Kg body weight of the subject. According to additional embodiments, the therapeutically effective amount of the exosomes ranges from about 1 mg to about 50 mg/Kg body weight of the subject.

According to another aspect, the present invention provides a composition comprising exosomes obtained from milk, wherein the composition is formulated for rectal administration, and wherein the exosomes comprise one or more miRNA molecules and TGF-β.

According to some embodiments, the milk is bovine, goat, or human milk. According to additional embodiments, the exosomes being obtained from a skim fraction of the milk and/or from a fat fraction of the milk. According to further embodiments, the milk is obtained before, during and/or after lactation. According to still further embodiments, the milk is pasteurized or not pasteurized. Each possibility represents a separate embodiment of the invention.

According to further embodiments, the one or more miRNA molecules contained or encapsulated in the exosomes of the composition are selected from the group consisting of let-7a, miR-320, miR-375, and miR-148a. Each possibility represents a separate embodiment of the invention. According to yet further embodiments, the miRNA molecules comprise let-7a, miR-320, miR-375, and miR-148a.

According to further embodiment, the TGF-β of the exosomes in the composition is TGF-β1.

According to still further embodiments, the exosomes of the composition further comprise at least one biologically active compound selected from the group consisting of proteins, peptides, nucleic acid molecules, and lipids.

According to yet further embodiments, the exosomes of the composition comprise less than about 20% (w/w) casein of the total protein of the exosomes.

According to some embodiments, the composition is formulated as an enema, suppository or foam. According to one exemplary embodiment, the composition is formulated as an enema which comprises a carrier and optionally a thickening agent and/or a lubricant. According to another exemplary embodiment, the composition is formulated as a suppository which comprises a carrier and a thickening agent.

According to another aspect, the present invention provides a method of treating inflammatory bowel disease (IBD) or a condition associated therewith comprising administering to a subject in need of such treatment a composition comprising a therapeutically effective amount of exosomes obtained from milk, wherein the exosomes comprise one or more miRNA molecules and TGF-β, and wherein the composition is administered by enteral route of administration, thereby treating IBD or the condition associated therewith.

According to some embodiment, the milk to be used for obtaining the exosomes for practicing the method of the present invention is bovine, goat, or human milk. According to additional embodiments, the exosomes to be used in practicing the method of the present invention are obtained from a skim fraction of the milk and/or from a fat fraction of the milk. According to further embodiments, the milk is obtained before, during and/or after lactation. According to still further embodiments, the milk is pasteurized or not pasteurized. Each possibility represents a separate embodiment of the invention.

According to further embodiments, the one or more miRNA molecules are selected from the group consisting of let-7a, miR-320, miR-375, and miR-148a. Each possibility represents a separate embodiment of the invention. According to yet further embodiments, the miRNA molecules comprise let-7a, miR-320, miR-375, and miR-148a.

According to some embodiments, the TGF-β of the exosomes to be used for practicing the method of the present invention is TGF-β1.

According to additional embodiments, the exosomes to be used further comprise at least one biologically active compound selected from the group consisting of proteins, peptides, nucleic acid molecules, and lipids.

According to further embodiments, the exosomes comprise less than about 20% (w/w) casein of the total protein of the exosomes.

According to still further embodiments, the inflammatory bowel disease (IBD) to be treated is selected from the group consisting of Crohn's disease and ulcerative colitis. Each possibility represents a separate embodiment of the invention.

According to yet further embodiments, ulcerative colitis is distal colitis.

According to still further embodiments, distal colitis is selected from the group consisting of proctitis, proctosigmoiditis, and left-sided colitis. Each possibility represents a separate embodiment of the invention.

According to one embodiment, the condition associated with IBD to be treated is pouchitis.

According to some embodiments, the composition is administered by oral administration or by tube feeding.

According to additional embodiments, the composition is administered by rectal administration.

According to further embodiments, the composition to be administered is formulated as a nutraceutical or pharmaceutical composition, a dietary formulation, or dietary supplement.

According to still further embodiments, the composition to be administered is formulated as an enema, suppository, or foam.

According to yet further embodiments, the therapeutically effective amount of the exosomes within the composition to be administered ranges from about 0.1 mg to about 250 mg/Kg body weight of the subject. According to still further embodiments, the therapeutically effective amount of the exosomes ranges from about 1 mg to about 50 mg/Kg body weight of the subject.

Other objects, features and advantages of the present invention will become clear from the following description and drawings.

BRIEF DESCRIPTION OF THE DRAWINGS

FIGS. 1A-K show characterization of exosomes isolated from cow or human milk. FIG. 1A shows the number of exosomes isolated from cow or human milk. FIGS. 1B and 1C show transmission electron microscopy analysis of cow or human MDEs, respectively, using negative staining. FIGS. 1D and 1E show nanosight analysis of cow or human MDE, respectively. FIGS. 1F and 1G show particle size distribution (by intensity) of cow or human isolated MDEs, respectively, by DLS. FIGS. 1H and 1I show protein expression of CD81 and CD9, as markers of exosomes, and HSP70, as a negative control, in cow or human milk derived exosomes, respectively. FIGS. 1J and 1K show the expression of miRNA-148 and miRNA-320 in cow or human MDE, respectively.

FIG. 2A is a Western blot analysis of the expression of CD81 and CD9 (exosome characteristic proteins), and HSP70 (negative control) in the exosomes isolated from the fat fraction of human milk. FIGS. 2B and 2C show transmission electron microscopy analysis of the exosomes isolated from the fat fraction of cow's milk. FIG. 2D shows qRT-PCR analysis of the expression of miRNA-148a-3p (miRNA-148) in exosomes isolated from cow's milk according to protocol A (A), protocol B (B), or protocol C (C).

FIGS. 4A-B show fluorescence images of exosomes distribution in mice administered by gavage with exosomes isolated either from cow milk (FIG. 4A) or human milk (FIG. 4B), and then labeled with the fluorescent dye DiR. FIG. 4C shows the weight of mice treated with exosomes isolated from cow or human milk during a seven days period. The weight of non-treated mice is also presented.

FIGS. 5A-D show representative colon sections from treated mice (DSS with or without exosomes; FIGS. 5D and 5B, respectively) or control mice (not treated with DSS with or without exosomes; FIGS. 5C and 5A), stained by H&E staining. FIG. 5E shows the histological score of the H&E stained sections of FIGS. 5A-D. FIG. 5F shows the disease activity index (DAI) in the tested groups.

FIGS. 6A and 6C show the weight of DSS-treated mice at day 1 of the DSS treatment (DSS D1) and at day 9 after seven days of DSS treatment followed by 2 days without DSS or exosomes (EXO−D9). FIGS. 6B and 6D show the weight of DSS-treated mice at day 1 of the DSS treatment (DSS D1) and at day 9 after seven days of DSS treatment followed by 2 days of treatment with exosomes isolated from cow's milk (EXO+D9; FIG. 6B) or from human milk (EXO+D9; FIG. 6D). FIGS. 6E-F show the effect of exosomes (EXO+) isolated from cow's milk (FIG. 6E) or from human milk (FIG. 6F) on the shortening of the colon. FIGS. 6G-H show the pathological score following treatment with exosomes (EXO+) isolated from cow's milk (FIG. 6G) or from human milk (FIG. 6H).

FIG. 7A shows Western blot analysis of TGF-β1 and β-actin protein level in colon of colitic mice non-treated (EXO−) or treated with milk derived exosomes (EXO+). FIG. 7B is a bar graph presenting the Western blot analysis results of FIG. 7A.

DETAILED DESCRIPTION OF THE INVENTION

Figure 1J:
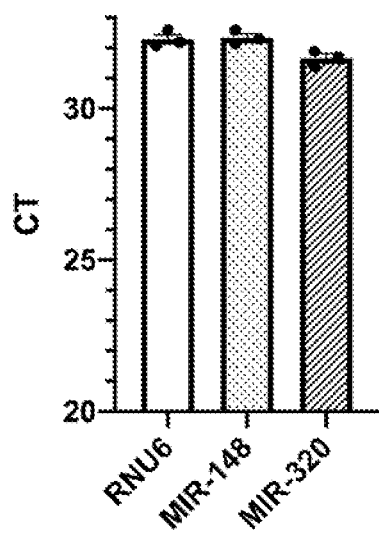

The present invention provides compositions comprising milk derived exosomes for use in treating inflammatory bowel disease (IBD) or a condition associated therewith, wherein the exosomes comprise or encapsulate one or more miRNA molecules and TGF-β, and wherein the compositions are formulated for enteral administration. The present invention further provides compositions comprising milk derived exosomes, wherein the composition is formulated for rectal administration, and wherein the exosomes comprise or encapsulate one or more miRNA molecules and TGF-β. The present invention further provides methods for treating IBD or a condition associated therewith comprising administering to a subject in need of such treatment a composition comprising one or more miRNAs and TGF-β, and wherein the composition is administered by enteral route of administration.

Definitions

The terms "milk" and "natural milk" are used interchangeably throughout the description and claims and refer to the nourishing liquid produced by the mammary glands of mature female mammals to provide nourishment for their young. The milk may be divided into two major fractions: a liquid fraction, termed herein "skim" (or "skim milk" or "skim fraction", or "skim milk fraction") and a "fat" fraction. The skim milk fraction is a milk fraction obtained after removal of milk fat. In some embodiments, the terms "whey", "whey fraction", "skim milk", "skim fraction" and "skim milk fraction" may interchangeably be used. In some embodiments, the skim fraction includes the whey fraction.

As used herein, the terms "treatment," "treating," and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment," as used herein, covers any treatment of a disease in a mammal, preferably a human, and includes: (a) reducing the incidence and/or risk of relapse of the disease during a symptom-free period; (b) relieving or reducing a symptom of the disease; (c) preventing the disease from occurring in a subject which may be predisposed to the disease but has not yet been diagnosed as having it; (d) inhibiting the disease, i.e., arresting its development (e.g., reducing the rate of disease progression); (e) reducing the frequency of episodes of the disease; and (f) relieving the disease, i.e., causing regression of the disease.

The term "exosome" refers to a type of microvesicle with a diameter of between 30 and 200 nm. Exosomes are either released from the cell when multivesicular bodies fuse with the plasma membrane or are released directly from the plasma membrane. An exosome may be obtained or isolated or derived from the skim fraction of milk (such as from the skim milk fraction) and/or from the fat fraction of milk.

The terms "microRNA" and "miRNA" are directed to a small non-coding RNA molecule that can function in transcriptional and post-transcriptional regulation of target gene expression.

The term "composition" as used herein refers to a composition which comprises the milk derived exosomes, and optionally a carrier and/or one or more excipients. The composition of the present invention is formulated for enteral administration.

The term "nutraceutical composition" as used herein refers to an edible composition isolated or purified from food which has a physiological benefit or provides protection or attenuation of a disease when orally administered. The nutraceutical composition may thus be presented in the form of a dietary formulation or supplement, either alone or admixed with edible foods or drinks.

The term "dietary formulation" includes, but is not limited to, complete dietary formulation, partial or incomplete dietary formulation, and disease or condition specific dietary formulation. A complete dietary formulation (i.e., which contains all the essential macro and micro nutrients, such as, proteins, carbohydrates, fat, vitamins, and minerals) can be used as a sole source of nutrition for the patient. Patients can receive 100% of their nutritional requirements from such complete dietary formulation. A partial or incomplete dietary formulation does not contain all the essential macro and micro nutrients and cannot be used as a sole source of nutrition for the patient. Partial or incomplete dietary formulation can be used as a dietary or nutritional supplement. A disease or condition specific dietary formulation is a formulation that delivers nutrients or pharmaceuticals and can be a complete or partial dietary formulation. The terms "enteral formula", "enteral nutrition formula" and "nutritional composition" have the same meaning as dietary formulation and are used interchangeably throughout the specification and claims. In some embodiments, the dietary formulation or supplement do not include miRNA molecules, other than the miRNA molecules encapsulated within the exosomes obtained or isolated form milk as disclosed herein.

The term "enteral administration" as used herein refers to any administration which involves the esophagus, stomach, small intestine and large intestine (i.e., the gastrointestinal tract). Methods of administration include oral, buccal, sublingual (dissolving the drug under the tongue), and rectal administration as well as tube feeding.

The term "tube feeding" refers to administration of a composition to a patient's gastrointestinal tract, other than through oral administration, including, but not limited to, through a nasogastric tube, a orogastric tube, a gastric tube, a jejunostomy tube (J-tube), percutaneous endoscopic gastrostomy (PEG), a port, such as a chest wall port that provides access to the stomach, jejunum and other suitable access ports.

The term "carrier" as used herein includes any material which, when combined with an active agent of a composition, allows the active agent to retain biological activity without causing disruptive reactions with the subject's immune system.

The term "pharmaceutically acceptable" means approved by a regulatory agency of the Federal or a state government or listed in the U. S. Pharmacopeia or other generally recognized pharmacopeia for use in animals, and more particularly in humans.

The term "Inflammatory bowel disease" (IBD) refers to a disease which involves chronic inflammation of all or part of the digestive tract. The term includes all kinds of IBD known in the art. IBD primarily includes Crohn's disease and ulcerative colitis.

The term "Crohn's disease" is characterized by inflammation present along the lining of the digestive tract, and often spreads deep into affected tissues. The inflammation caused by Crohn's disease can involve different areas of the digestive tract from the mouth to the anus. The most common areas affected by Crohn's disease are the last part of the small intestine called the ileum and the colon Inflammation may be confined to the bowel wall, which can lead to scarring (stenosis), or inflammation may spread through the bowel wall (fistula). Signs and symptoms of Crohn's disease can range from mild to severe and may develop gradually or come on suddenly, without warning. Signs and symptoms include, without limitation, diarrhea, abdominal pain and cramping, nausea and vomiting, blood in the stool, ulcers on the surface of the intestine or in the mouth, reduced appetite and weight loss, fever, fatigue, arthritis, eye inflammation, skin disorders, inflammation of the liver or bile ducts, and delayed growth or sexual development (in children).

The term "Colitis" refers to inflammation of the inner lining of the colon. Various types of colitis are known, designated according to the cause of the disease, including, but not limited to, ulcerative colitis, Crohn's colitis, diversion colitis, ischemic colitis, infectious colitis, fulminant colitis, collagenous colitis, chemical colitis, microscopic colitis, lymphocytic colitis, Behçet's disease, indeterminate colitis, and a typical colitis. Each possibility represents a separate embodiment of the invention.

Ulcerative Colitis (UC) is characterized in long-lasting inflammation in the colon. Symptoms usually develop over time, rather than suddenly. Ulcerative colitis typically affects only the innermost lining of the large intestine (colon) and rectum. It occurs through continuous stretches of the colon. Ulcerative colitis is categorized to: proctitis which involves only the rectum, proctosigmoiditis which involves the rectum and sigmoid colon, left-sided colitis which involves the extending as far as the descending colon or splenic flexure, and pancolitis. Each possibility represents a separate embodiment of the present invention.

The term "pouchitis" as used herein refers to an inflammation of the ileal pouch (an artificial rectum surgically created out of ileal gut tissue in patients who have undergone a colectomy), which is created in the management of patients with ulcerative colitis, indeterminate colitis, or other types of colitis.

The term "therapeutically effective amount" of an active agent is that amount of the agent which is sufficient to provide a beneficial effect to the subject to which the agent is administered. An effective amount of the compound may vary according to factors such as the disease state, age, sex, and weight of the individual.

Exosomes and Methods of Preparation

The present invention provides exosomes obtained from milk and use thereof for treating IBD or a condition associated therewith.

The exosomes of the present invention are obtained from milk by methods which comprise fractionating the milk and obtaining a skim fraction and a fat fraction. The exosomes of the present invention can be obtained/isolated from the skim fraction and/or from the fat fraction of the milk.

According to some embodiments, milk is fractionated by centrifugation at 5000 g-6500 g for 30 minutes at 4° C. Two fractions are obtained from the milk: a fat fraction and a skim milk fraction. The skim fraction is centrifuged at 12000 g for 1 hour at 4° C. Next, the supernatant may be filtered through filters (for example, 0.45 and 0.22 µm filters). The filtered supernatant may then be ultra-centrifuged at 50000-100000 g (for example, at 70000 g) for 30-120 minutes (for example, for 30 minutes) at 4° C. to precipitate casein. The pellet may be discarded and the supernatant may be ultra-centrifuged for any number of times, for example, once or twice, at 80000-150000 g (for example at 135000 g), for 30-180 minutes (for example, 90 minutes) at 4° C. The resulting pellet includes milk exosomes obtained/isolated from the skim milk fraction.

According to some embodiments, there is provided a method for obtaining exosomes from milk, the method comprising centrifugation of milk at 1000-8000 g (for example, 5000 g-6500 g) for 30 minutes at 4° C., to obtain two fractions of milk: a fat fraction and a skim milk fraction. The fat fraction is processed by cycles of cooling-heating (2-4 cycles) from −80° C. or −20° C. to 37° C. and 60° C. Next, the fat layer may then be centrifuged at 8000-15000 g (for example, at 10000 g) for 10-30 minutes (for example, for 10 minutes) at 4° C. At this point, the pellet may be discarded and the supernatant may be filtered through filters (for example, a 0.45 and/or 0.22 µm filters), and the filtered solution may be ultra-centrifuged at 80000-100000 g (for example, at 100000 g) for 30-90 min (for example, for 60 min). The pellet is discarded and the supernatant is centrifuged at 135000 g for 90 minutes at 4° C. The resulting pellet includes the isolated exosomes from the fat fraction.

According to the present invention, the exosomes obtained by these methods are advantageous as they are safe for further use. The isolation of exosomes involves centrifugation and filtration steps in the presence of a suitable buffer (such as, PBS) which is used as a washing reagent, and/or acetic acid and/or sodium citrate, and does not involve other reagents or devices that may render the process expensive and less safe. The exosomes obtained by these methods can be readily added to enteral formulas, to supplement such formulas. Further, such exosomes can provide a preventative and/or therapeutic effect of IBD or a condition associated therewith.

The milk may be obtained from various suitable sources, including, but not limited to, bovine (cow), goat, human, camel, and the like. In some embodiments, the milk may be obtained at various time points before, during and/or after lactation. The milk may be obtained at various time points during the day (for example, morning, evening, midnight). The milk may be obtained at various time points after birth.

The exosomes can be obtained from bovine (cow) milk, before or after pasteurization. The exosomes can be obtained from the skim fraction and/or fat fraction and/or whey fraction of the cow milk. Each possibility is a separate embodiment of the invention.

The exosomes may be obtained from goat milk or camel milk, before or after pasteurization. The exosomes may be obtained from the skim fraction and/or fat fraction and/or whey fraction of the goat or camel milk. Each possibility is a separate embodiment of the invention.

The exosomes may be obtained from human female breast milk. The exosomes may be obtained from the skim fraction and/or fat fraction and/or whey fraction of the human milk.

The human milk may be obtained from breast milk of a term baby mother and/or from the breast milk of a pre-term baby mother. Each possibility is a separate embodiment of the invention.

The identity and/or relative abundancy of the molecules within the exosomes may be identical or different between exosomes obtained from milk of different sources. Additionally or alternatively, the identity and/or relative abundancy of the miRNAs may be identical or different between exosomes isolated from milk obtained at different times of the day.

According to the principles of the present invention, the exosomes disclosed herein comprise or encapsulate or enclose one or more miRNA molecules and TGF-β. The exosomes can further comprise or encapsulate additional biological components, including nucleic acids, proteins, peptides, lipids, minerals, hormones, and the like.

In some embodiments, the exosomes comprise/encapsulate/include one or more miRNA molecules selected from the group consisting of let-7b, mir-320, miR-375, and miR-148a. Each possibility is a separate embodiment.

In some embodiments, the exosomes comprise or encapsulate let-7b, mir-320, miR-375, and miR-148a. In some embodiments, the exosomes further comprise one or more of the miRNA molecules selected from the group consisting of miR-26, miR-99, miR-30, let-7a, miR-146, and miR-200. Each possibility is a separate embodiment.

In some embodiments, the exosomes comprise or encapsulate TGF-β1. In some embodiments, the exosomes comprise annexin A1 and/or mucin-1. Each possibility is a separate embodiment.

In some embodiments, the exosomes include less than about 20% casein of the total protein of the exosomes. In some embodiments, the exosomes include less than about 10% casein of the total protein of the exosomes. In some embodiments, the exosomes include less than about 5% casein of the total protein of the exosomes. In some embodiments, the exosomes include less than about 2% casein of the total protein of the exosomes. In some embodiments, the exosomes include less than about 1% casein of the total protein of the exosomes. In some embodiments, the exosomes are essentially devoid of casein.

In some embodiments, the exosomes may be added to the composition in a dehydrated form. In some embodiments, the exosomes may be added to the composition in a lyophilized form. In some embodiments, the exosomes may be added to the composition in any appropriate form.

Enteral Compositions

The present invention provides compositions comprising milk derived exosomes, wherein the compositions are formulated for enteral administration. The compositions can be formulated for oral, buccal, sublingual, or rectal administration, or for tube feeding.

The compositions can take the form of solutions, suspensions, emulsions, tablets, capsules, powders, sustained-release formulations, and the like. The compositions can be formulated for rectal administration as an enema, suppository, depot tablets (controlled release tablets), or foam.

The compositions formulated as tablets or capsules can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin.

The compositions can be formulated as a dietary formulation or supplement comprising the exosomes obtained or isolated from milk. The dietary formulation or supplement can further comprise additional components such as a source of protein, a source of carbohydrate, one or more essential fatty acids, a source of vitamins and minerals, and an emulsifier. The source of carbohydrates can be any simple or complex carbohydrate, e.g., monosaccharides, disaccharides, or oligosaccharides. The source of carbohydrate can be corn starch, dextrose, glucose, or combination thereof. The source of protein can be any protein, protein hydrolysate, peptide mixtures, or amino acid mixtures, e.g., milk, egg, soy or meat proteins. The protein hydrolysate can be partially hydrolyzed in nature and include a substantial fraction of variable chain length peptides. In some embodiments, only the highest biological value proteins are hydrolyzed, e.g., whey, lactalbumin, casein, egg white, egg solids, or soy. In some embodiments, the protein source is lactose-free, and free amino acids are avoided in the formulation. The dietary formulation or supplement can further comprise vitamins and minerals in accordance with the Recommended Dietary Allowance (RDA), now called the Daily Reference Intake (DRI). The dietary formulation or supplement can further comprise an emulsifier or other inactive ingredients such as sweeteners and/or flavorings, which can be artificial. According to one exemplary embodiment, the dietary formulation or supplement is in the form of a powder that is to be reconstituted with a liquid.

When formulated as solutions, suspensions or emulsions, the compositions can comprise, for example, water or phosphate buffer saline (PBS), and the like, as a carrier. Such solutions, suspensions or emulsions which comprise the milk-derived exosomes can be packaged in either single dose or multidose packages for administration by feeding tube.

The composition can be formulated for rectal administration. For example, enema compositions comprise an effective amount of milk derived exosomes in a suitable carrier, such as water, phosphate buffered saline (PBS), alcohol, or an aqueous-alcoholic fluid. The composition is preferably thickened with natural or synthetic thickeners or gelling agents such as gums, acrylates, carbomers, or modified celluloses. The compositions can also comprise an effective amount of a lubricant such as a natural or synthetic fat or oil, i.e., a tris-fatty acid glycerate or lecithin. Nontoxic nonionic surfactants can also be included as wetting agents and dispersants. Unit dosages of enema compositions can be administered from prefilled bags or syringes. The compositions may also comprise an effective amount of a foaming agent such as n-butane, propane or isobutane. Such compositions can be delivered from a preloaded syringe pressurized container, so that the composition is delivered to the colon as a foam, which inhibits its escape from the target site.

When the composition is to be administered as an enema, it need only be dissolved or dispersed in a small volume, such as 100 ml or less, of a liquid such as an aqueous mixture. It is preferable to make the composition isotonic, to avoid any upset in the water balance of the affected tissues. Thus, the carrier for an enema can be physiological buffered saline. It may be convenient to prepare an enema composition as a solid, comprising a dose of the exosomes with appropriate quantities of a buffering agent, to be reconstituted with, for example, deionized water at the time of use. Alternatively, the enema may be stored as a liquid, for example in PBS, and administered in that form.

Suppositories, in general, are usually prepared from low-melting solid materials, which are administered in a solid form and melt in the rectum, to release the active agent which is dispersed in the solid matrix. Traditionally, the solids from which suppositories were made were oily or waxy materials, such as cocoa butter and the like. Bland petroleum and vegetable waxes have also been used, as have mixtures of vegetable oils thickened with such waxes. The availability of gelling agents enables such formulations to be prepared in aqueous-based materials, avoiding the administration of oily and waxy materials, which, are quite foreign to the body. Such an aqueous-based suppositories can be prepared by dissolving or suspending the exosomes in water, preferably made isotonic by addition of appropriate inorganic salts, and thickening the mixture by the addition of a thickening or gelling agent such as gums or modified cellulose, until the composition becomes a soft solid at room temperature but will liquefy at the temperature of the body. The problem of balancing the melting temperature of suppositories is easily reduced by labelling the product to be stored under refrigeration.

According to the principles of the present invention, the exosomes added to the composition preserve at least part of the biological activity and/or chemical stability of the components included therewith.

The composition of the present invention can comprise one or more drugs known to alleviate or relieve IBD or a condition associated therewith. Examples of such drugs include anti-inflammatory agents including, but not limited to, corticosteroids and aminosalicylates, such as mesalamine, balsalazide, and olsalazine; immunosuppressant drugs including, but not limited to, azathioprine, mercaptopurine, cyclosporine, and methotrexate; Tumor necrosis factor (TNF)-α inhibitors; biologic agents that neutralize TNF-α; and antibiotics.

Methods of Treatment

The present invention provides compositions comprising milk-derived exosomes for use in treating or preventing IBD or a condition associated therewith, wherein the exosomes comprise one or more miRNA molecules and TGF-β, and wherein the compositions are formulated for enteral administration. The present invention further provides methods of treating or preventing IBD or a condition associated therewith, comprising administering to a subject in need of such treatment a composition comprising a therapeutically effective amount of milk derived exosomes, wherein the exosomes comprise one or more miRNA molecules and TGF-β, and wherein the composition is administered by enteral route of administration, thereby treating or preventing IBD.

According to some embodiments, the IBD is selected from the group consisting of Crohn' disease and colitis. According to additional embodiments, colitis includes, but is not limited to, ulcerative colitis, diversion colitis, ischemic colitis, infectious colitis, fulminant colitis, collagenous colitis, chemical colitis, microscopic colitis, lymphocytic colitis, Behçet's disease, indeterminate colitis, and a typical colitis. Each possibility represents a separate embodiment of the present invention.

According to further embodiments, ulcerative Colitis (UC) includes proctitis, proctosigmoiditis, left-sided colitis, and pancolitis. Each possibility represents a separate embodiment of the present invention.

According to still further embodiments, a condition associated with IBD is pouchitis. According to yet further embodiments, the condition associated with IBD is Familial adenomatous polyposis (FAP).

Signs and symptoms of Crohn's disease include, without limitation, diarrhea, abdominal pain and cramping, nausea and vomiting, blood in the stool, ulcers on the surface of the intestine or in the mouth, reduced appetite and weight loss.

Other complications outside the gastrointestinal tract may include anemia, skin rashes, arthritis, inflammation of the eye, and tiredness.

Common symptoms of colitis include, without limitation, mild to severe abdominal pains and tenderness (depending on the stage of the disease), persistent hemorrhagic diarrhea with pus either present or absent in the stools, fecal incontinence, flatulence, fatigue, loss of appetite and weight loss. The primary symptoms of ulcerative colitis are abdominal pain and diarrhea mixed with blood. Weight loss, fever, and anemia may also occur.

The methods of the present invention are useful for preventing or treating IBD or one or more symptoms associated therewith. It is noted that treating of IBD or one or more symptoms associated therewith results in a decrease in the Disease Activity Index (DAI) value of said subject.

The methods of the present invention can be used as a combination therapy. Thus, the compositions of the present invention can be administered prior to, simultaneously, or subsequently to a drug known to alleviating and/or relieving IBD.

According to some embodiments, the composition is administered once a day, twice a day, three times a day or four times a day for at least one day, at least one week, for at least one month, or so long as treatment is achieved. Alternatively, the composition is administered once every other day, once every three days, once a week for a week, a month, or so long as treatment is achieved.

According to some embodiments, the therapeutically effective amount of the exosomes in the composition ranges from about 0.1 mg to 250 mg/Kg of body weight of a subject in need of such treatment According to some embodiments, the preventative and/or therapeutic effect of IBD is not achieved by a dietary formulation or enteral formula which does not include the exosomes isolated from milk.

The terms "comprises", "comprising", "includes", "including", "having" and their conjugates mean "including but not limited to". The term "consisting of" means "including and limited to". The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein the term "about" in reference to a numerical value stated herein is to be understood as the stated value +/−10%.

As used herein, the singular form "a", "an" and "the" include plural references unless the context clearly dictates otherwise. For example, the term "a compound" or "at least one compound" may include a plurality of compounds, including mixtures thereof.

It is to be noted that each possibility disclosed throughout the specification and claims represents a separate embodiment of the invention.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

The following examples are presented to provide a more complete understanding of the invention. The specific techniques, conditions, materials, proportions and reported data set forth to illustrate the principles of the invention are exemplary and should not be construed as limiting the scope of the invention.

EXAMPLES

Methods
Isolation of Milk Derived Exosomes from the Skim Fraction or from the Fat Fraction of Milk Exosomes were isolated from the skim fraction of human or cow milk by different protocols.

From human milk: Exosomes were isolated by sequential ultracentrifugation and filtration. The milk samples were fractionated by centrifugation at 6500 g for 30 min at 4° C. Two fractions were obtained from each sample: the fat and skim milk. The exosomes were isolated from the skim fraction. The skim milk was centrifuged at 12000 g for 1 hour at 4° C. to remove debris. The skim was then passed through 0.45 μm and 0.22 μm filters to remove residual debris. The filtered supernatant was centrifuged at 135000 g for 90 min at 4° C. to pellet the exosomes.

From cow milk: There are two class of proteins in milk: caseins and whey. Human milk contains those proteins in a ratio of 40:60, respectively; while in cow's milk contains casein and whey proteins in a ratio of 80:20. As cow's milk contains considerably more casein than human milk, the isolation of exosomes from cow's milk was performed similarly to the protocol of human milk described above, with one modification. Following filtrations, the skim was centrifugated at 70000 g for 30 min at 4° C. to discard casein. The supernatant was centrifugated at centrifugated at 135000 g for 90 min at 4° C. to pellet the exosomes.

The exosomes pellet was left overnight in PBS for 4° C. to dissolve the exosomes. MDE were filtered through a 0.22 μm filter. The protein content of the exosomes preparation was measured by a BCA protein assay (Thermo).

In other experiments, isolation of exosomes from skim milk fraction was performed as follows:

Protocol A—this protocol used acetic acid and citric acid to control the pH. In step 3 of the protocol, acetic acid and sodium citrate were added at a concentration of 0.1% to 1% for 0 to 5 minutes of incubation at room temperature and at 4° C.:
1. Natural milk (2 ml-150 ml) was centrifuged at 5000 g for 30 minutes at 4° C. The separated fat fraction was removed and the liquid phase skim milk was used in step 2.
2. The liquid phase skim milk was centrifuged at 12000 g for 60 minutes at 4° C. The pellet which contained debris was discarded and the supernatant (sup) was used in step 3.
3. The sup was incubated with 0.1% to 1% acetic acid or sodium citrate (0-5 minutes) at 4° C. and at room temperature (RT).
4. After the incubation step, the sup was centrifuged at 100000 g for 10 minutes at 4° C. The pellet (which contained casein) was discarded and the sup was used in the next step.
5. The sup was filtrated using a 0.22 □m filter and the filtered liquid was centrifuged at 135000 g for 90 minutes at 4° C. 1. The resulting pellet included the isolated exosomes.

Protocol B—this protocol used filters during the isolation of the exosomes:
1. Natural milk was centrifuged at 5000 g for 30 minutes at 4° C. The separated fat fraction was removed and the liquid phase skim milk was used in step 2.
2. The liquid phase skim milk was centrifuged at 12000 g for 60 minutes at 4° C. The pellet, which contained debris was discarded and the supernatant (sup) was used in step 3.
3. The sup was filtered using an 0.45 μm filter and the filtered liquid was filtered again using 0.22 μm filter. The resulting filtered liquid was centrifuged at 100000 g for 60 minutes at 4° C. The pellet (which contained casein) was discarded and the sup was used in the next step.
4. The sup was centrifuged at 135000 g for 90 minutes at 4° C.
5. The resulting pellet included the isolated exosomes.

Protocol C—Isolation of Milk Derived Exosomes from the Fat Fraction of Milk:
1. Natural milk was centrifuged at 5000 g for 30 minutes at 4° C. The separated fat fraction was used for further processing and the liquid phase skim milk was removed.
2. The fat milk fraction was subjected to cycles of cooling-heating (2-4 cycles) from −80° C. or −20° C. to 37° C. and 60° C. As a result of the cooling-heating cycles the fat was dissolved in PBS.
3. The solution was then filtered using a 0.22 μm filter and the filtered solution was centrifuged at 100000 g for 60 minutes at 4° C.
4. The pellet was discarded and the supernatant was centrifuged at 135000 g for 90 minutes at 4° C. to pellet the exosomes.
5. The protein content of the exosomes preparation was measured by a BCA protein assay (Thermo).

Electron Microscopy

Exosomes were analyzed by electron microscopy using negative staining. Isolated exosomes were stained with 2% phosphotungstic acid (PTA) in water. Briefly, 5 μl of diluted exosomes in PBS were placed on Formvar/carbon coated copper 200 mesh grids (EMA) and mixed with 5 μl PTA for 10-20 seconds. Excess stain was removed and the grids were dried. Samples were examined with a Jem-1400 Plus transmission electron microscope (Jeol, Peabody, MA, USA).

Nanoparticle Analysis

Nanoparticle tracking analysis (NTA), performed with NS300 nanoparticle analyzer (NanoSight, Malvern, Worchestershire, UK), was used to measure the size distribution of MDE. A suspension of MDE in PBS was loaded into the sample chamber of the Nanosight unit, and video was recorded for 60 sec with a frame rate of 24.98 fps. The blue laser source at 488 nm was applied to the diluted MDE suspension. The particle movement was analyzed by NTA software (version 3.2, NanoSight). All the measurements were performed at 22° C. in light scatter mode.

Dynamic Light Scattering (DLS)

DLS and zeta potential determinations were performed with a Zetasizer nanoseries instrument (Malvern Nano-Zetasizer, $\lambda=532$ nm laser wavelength). The exosome size data refers to the scattering intensity distribution (z average).

DiR-Labelled MDEs

MDE were incubated with 1 μM fluorescent lipophilic tracer DiR (1,1-dioctadecyl-3,3,3,3-tetramethylindotricarbocyanine iodide; Invitrogen, Life Technologies) at 37° C. for 15 min. At the end of the incubation PBS was added, centrifugation at 100000 g for 60 min was performed, the labelled exosomes were pelleted, and the unbound label was discarded.

DSS-Induced Colitis in Mice

DSS administration is the most widely used animal model to study colitis due to its simplicity, reproducibility, and uniformity. The DSS model exhibits many symptoms similar to those seen in human colitis, such as diarrhea, bloody feces, body weight loss, mucosal ulceration, and shortening of the colon. Two protocols were used: a preventive protocol and the treatment protocol.

Preventive protocol: colitis was induced in eight weeks Balb/c mice by adding 5% DSS into the drinking water from day 1. Control mice received regular drinking water. Mice treated with DSS or control mice were either treated for 7 days with human milk derived exosomes (EXO) at a dose of 0.5 mg/ml per mouse in 200 µl PBS by gavage or administered PBS only. The weight and the disease activity index (DAI) of the mice were monitored. The DAI score was used to evaluate daily the clinical progression of colitis. The DAI is a combined score of weight loss, stool consistency, and bleeding. The scores were defined as follows: weight loss: 0 (no loss), 1 (1-5%), 2 (5-10%), 3 (10-20%), and 4 (>20%); stool consistency: 0 (normal), 2 (loose stool), and 4 (diarrhea); bleeding: 0 (no blood), 1 (visual pellet bleeding), and 2 (gross bleeding, blood around anus); prolapse; 0 (none), 1 (signal of prolapse), 2 (prolapse), 3 (extended prolapse). Histologic score was determined based on the following parameters: lateral extension inflammation (0-4), in depth inflammation grade (0-4), lateral extension necrosis/ulceration (0-4), and in-depth necrosis/ulceration (0-4).

Treatment protocol: colitis was induced in eight weeks Balb/c mice by adding 5% DSS in the drinking water for seven days. The mice were euthanized when excessive suffering, moribund, or weight loss ≥20% appeared. The mice were evaluated daily from the beginning of the DSS treatment. After one week of DSS treatment, the water was changed to regular water. The mice received orally for 6 days a gavage of 0.5 mg/mouse of MDE from human or cow milk in 200 µl PBS. At the end of the experiment, the mice were sacrificed, and their colon was removed, analyzed for its outward appearance, and its length was measured. After removing cecum and adipose tissue, the colon was cut to 3 parts: the proximal, middle and distal parts. The distal part (2 cm) was fixed in a 4% formalin solution, embedded in paraffin, stained with H&E, and examined under light microscope. Histological scoring was determined. Cell differentiation, hemorrhages, fibrin deposition, and lesion distribution were also evaluated. The proximal and middle part of the colon were frozen in liquid nitrogen and stored until use at −80° C. for protein, gene and miRNA expression analysis.

For protein analysis, stainless steel beads (5 mm mean diameter) and 200 µl of RIPA buffer with prolinase inhibitor cocktail were added to a section of the colon tissue. The tissue was homogenized on the TissueLyser5. The sample was centrifuge briefly to precipitate the tissue debris. The protein content was measured by a BCA protein assay (Thermo). Gene and miRNA expression analysis in the colon tissue was performed after RNA extraction.

Extraction of Total RNA
From Exosomes

Trizol reagent (INVITROGEN, Carlsbad, USA) was added to the pellet of isolated MDEs. Chloroform was added, the mixture was shaken vigorously and incubated for 15 min at room temperature, and then centrifuged at 12000 g for 15 min at 4° C. The aqueous phase was transferred to a new tube. Subsequently, isopropanol (0.5 ml per 1 ml Trizol reagent) was added to precipitate the RNA, and the solution was mixed by inversion. After incubation for 10 min at room temperature, the samples were centrifuged at 12000 g for 10 min at 4° C. The supernatant was discarded, and the pellet was washed with 75% ethanol (1 ml per Trizol reagent) and centrifuged at 12000 g for 5 min at 4° C. The pellet was air dried and resuspended in 20 µl of RNase-free water.

From Colon Tissue.

Stainless steel beads (5 mm mean diameter) and 300 µl of Trizol reagent were added to a section of the colon tissue. The tissue was homogenized on the TissueLyser5. The sample was centrifuge briefly to precipitate the tissue debris. The RNA isolation was performed on the supernatant using Zymo Direct-zol RNA MiniPrep Kit (Zymo Research, Irvine, CA) according to the manufacturer's instructions.

RNA quantity and quality were assessed by measuring the absorbance at different wavelengths using a NanoDrop spectrophotometer of the RNA samples.

MicroRNA Detection by qRT-PCR

Total RNA samples: 500 ng of total RNA (extracted from colon tissue) and 100 ng (extracted from MDE), were used to prepare cDNA using the qScript microRNA cDNA Synthesis Kit (QuantaBio, Beverly, MA, USA). After cDNA synthesis, an equivalent of 2.4 ng of the original RNA sample was mixed with Perfecta SYBR Green SuperMix (QuantaBio) and Universal PCR Primers (QuantaBio) in 15 µl qPCR reactions. Three or two cDNA samples were run in adjacent wells of each 96-well qPCR plate. The qPCR plates were run using the StepOnePlus Real-Time PCR System (Applied Biosystems) using a two-step cycling protocol (95° C. for 5 min followed by 40 cycles of 95° C. for 5 seconds and 60° C. for 30 seconds), concluding with a melting curve. After the reactions were completed, Ct values were determined using fixed-threshold settings. The $2^{-\Delta\Delta CT}$ method was used to determine the relative amounts of miRNAs.

Quantitation of mRNA by qRT-PCR

The Expression of miRNA-148a-3p (mir-148a) in the exosomes was analyzed by qRT-PCR. The qRT-PCR results were calculated by the Delta-Delta CT method $2^{-\Delta\Delta Ct}$, and the values were normalized against RNU6B (Primers used: miR-148a-3p: CGCTCAGTGCACTACAGAACTT-TT (SEQ ID NO: 1), RNU6 (NR_002752.1): GCAAAT-TCGTGA AGCGTTCC) (SEQ ID NO: 2).

cDNA for the quantification of mRNA was generated using the high capacity RNA-cDNA kit (Applied Biosystems, Foster City, CA, USA) according to the manufacturer's instructions.

Total RNA isolated from colon tissue (1 µg) was used to generate cDNA. The cDNA was subjected to qPCR. The mRNA levels of IL-6 and TNF-α were measured using qRT-PCR with master mix (Fast qPCR SyGreen Blue Mix, PCR Biosyntesis, Pennsylvania, USA) using a StepOne Plus Real-Time PCR System machine (Applied Biosystems). Primers:

```
TNF-α:
                                    (SEQ ID NO: 3)
For 5'-GTTCTGTCCCTTTCACTCAC, (SEQ ID NO: 4)
Rev 5'-TGCCTCTTCTGCCAGTTC;

IL-6:
                                    (SEQ ID NO: 5)
For 5'- GAGTCACAGAAGGAGTGGCTAAGGA, (SEQ ID NO: 6)
Rev 5'-CGCACTAGGTTTGCCGAGTAGATCT;

GAPDH:
                                    (SEQ ID NO: 7)
For 5'-GCCTTCCGTGTTCCTACC, (SEQ ID NO: 8)
Rev 5'-CTTCACCACCTTCTTGATGTC.
```

The PCR reaction steps were 1 cycle at 95° C. for 5 min, 40 cycles of 95° C. for 5 seconds, and 60° C. for 30 seconds. The $2^{-\Delta\Delta CT}$ method was used to determine the relative amounts of mRNA.

Immunoblotting

Proteins were run on SDS-PAGE and then transferred onto a PVDF membrane. The membranes were probed with antibodies and detected using enhanced chemiluminescence detection reaction. Primary antibodies were as follows: anti-CD9 (1:1000; SBI System Biosciences, Palo Alto, CA, USA), anti CD81 (1:1000; Cosmo Bio, Tokyo, Japan), anti HSP70 (1:1000; SBI System Biosciences, Palo Alto, CA, USA), rabbit anti TGF-β1 (Abcam, Cambridge, MA, USA), rabbit anti β-actin (Abcam, Cambridge, MA, USA). The secondary antibody was horseradish peroxidase (HRP)-conjugated goat anti-mouse or anti-rabbit (1:3000; Cell Signaling Technology). Quantification was performed using NIH-Image software (http://rsb.info.nih.gov/nih-image/download.html).

Example 1

Isolation and Characterization of Exosomes in the Skim or Fat Fractions of Cow or Human Milk There are two class of proteins in milk: caseins and whey. Human milk contains casein and whey proteins in a ratio of 40:60, respectively; while cow's milk contains these proteins in a ratio of 80:20, respectively. As the amount of total protein in cow's milk is more than double that of human milk, cow's milk contains considerably more casein than human milk. Milk derived exosomes were isolated from the skim fraction of cow or human milk. Due to the different amount of casein in cow or human milk, the isolation of exosomes from cow or human milk was performed using the protocols described herein above.

As seen in FIGS. 1A-K, the vesicles isolated from cow or human milk were similar and identified as exosomes. Transmission electron microscopy analysis showed that the nanovesicles isolated from cow or human milk have a typical round or cup shape appearance (FIGS. 1B and 1C, respectively). Different methodologies were applied to confirm the size of the vesicles isolated from milk. For instance, nanoparticle tracking analysis (NTA), a conventional method of characterizing exosomes, was exploited to measure the exosome size based on the tracking of Brownian movement. The mean size was 179 nm for the vesicles isolated from cow milk and 166 nm from those isolated from human milk (FIGS. 1D and 1E, respectively). Dynamic light scattering (DLS) was also applied to measure the size of the exosomes by Z-average. Exosome size determined by DLS was found to be 131 nm and 96.91 nm for vesicles isolated from cow or human milk, respectively (FIGS. 1F and 1G, respectively). The polydispersity index (PDI) was also evaluated by DLS to characterize the size distribution of the exosomes. The PDI was 0.281 for the vesicles isolated from cow milk and 0.261 for those isolated from human milk (FIGS. 1F and 1G, respectively), showing relatively even size distribution of the exosomes which could also be confirmed by the sharp single peak in NTA analysis. According to these results, the size of the vesicles isolated from cow or human milk is the characteristic size of exosomes.

Exosomes purity was assessed by Western blot analysis. As shown in FIGS. 1H and 1I, the exosomes isolated from cow or human milk expressed exosome-related proteins, i.e., CD9 and CD81, while HSP70, a control protein, was only detected in the total cellular lysate and not in the exosomes, indicating that the isolated exosomes were highly purified and were not contaminated by abundant intracellular components and debris.

Figure 1K:
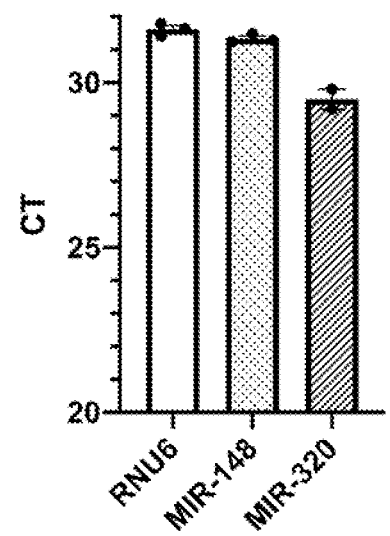

One main cargo of exosomes are MiRNAs. Indeed, several miRNAs such as miR-148 and miR320 were isolated from cow or human milk by qRT-PCR (FIGS. 1J and 1K, respectively).

Taken together, these results demonstrated that exosomes isolated from cow or human milk were of high purity.

Isolation of exosomes from the fat fraction of milk was next performed.

Figure 2A:
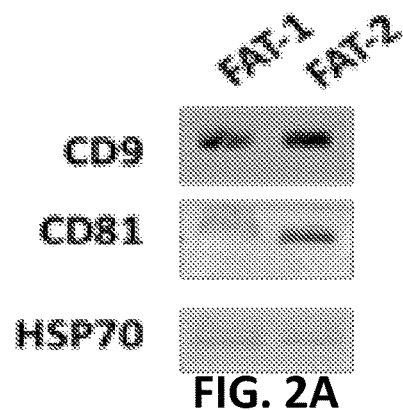
FIGS. 2A-D show analysis of the exosomes isolated from the fat fraction of milk.
Figure 2B:
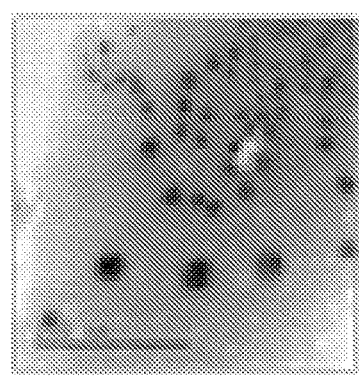
Figure 2C:
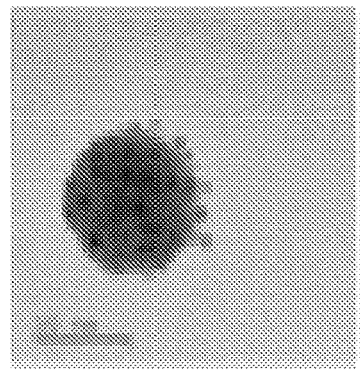

FIG. 2A shows the expression of the exosome characteristic proteins, i.e., CD81 and CD9, by Western blot analysis in exosomes isolated from the fat fraction of cow's milk according to Protocol C. HSP70 was not detected in these fractions. FIGS. 2B-C show transmission electron microscopy analysis of the exosomes isolated from the fat fraction of cow's milk.

Figure 2D:
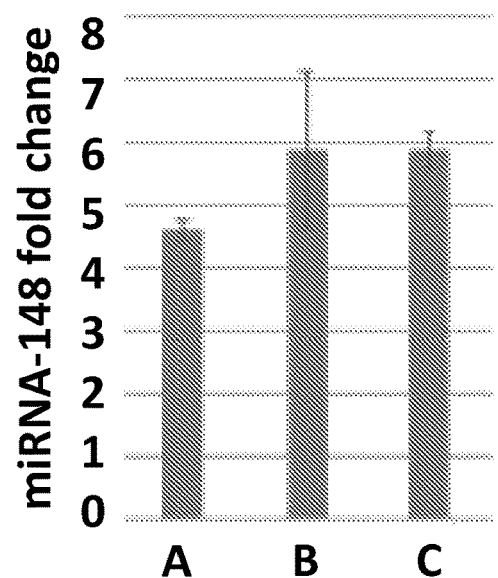

The expression of miRNA-148a-3p (miRNA-148) in the exosomes isolated from cow's milk according to protocols A, B or C was analyzed by qRT-PCR. The qRT-PCR results were calculated by the Delta-Delta CT method $2^{\wedge}(-\Delta\Delta Ct)$, and the values were normalized against RNU6B. The results shown in FIG. 2D indicated that the exosomes, whether isolated from the skim or fat fractions of cow's milk, contained miRNA molecules, e.g., miR-148.

Figure 3:
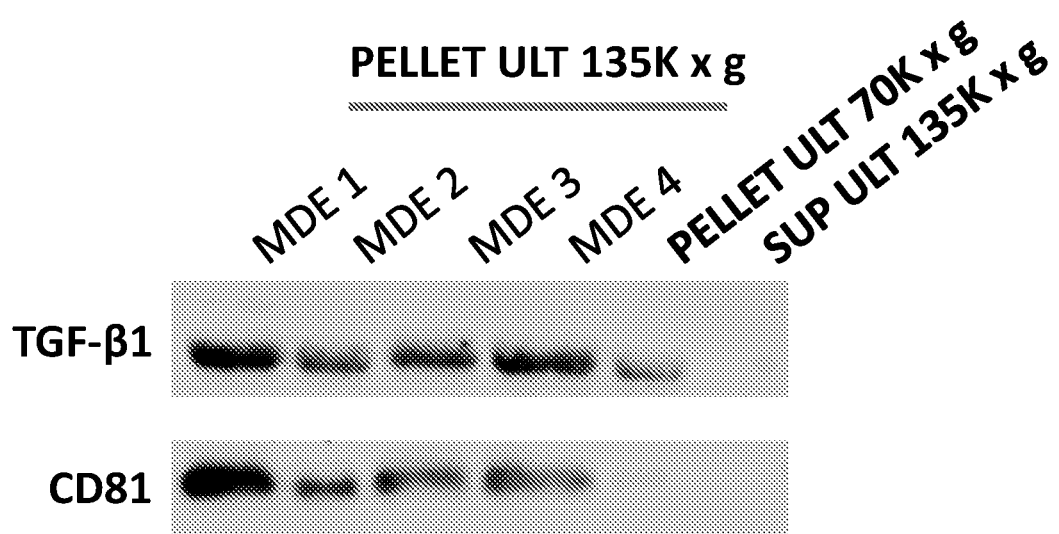
FIG. 3 shows Western blot analysis of TGF-β1 and CD81 in milk derived exosomes (MDE) isolated from several batches of cow's milk, in the pellet following ultracentrifugation (ULT) at 70,000 g, and in the supernatant following ultracentrifugation at 135,000 g.

The next aim was to determine whether the milk derived exosomes contain anti-inflammatory polypeptides. As a candidate, TGF-β1, a protein known for its anti-inflammatory activity in the colon, was evaluated. As shown in FIG. 3, TGF-β1 was found to be highly expressed in milk derived exosomes (MDE) as compared to other milk fractions such as the pellet following ultracentrifugation at 70,000 g or the supernatant following ultracentrifugation at 135,000 g (FIG. 3).

Altogether, these results demonstrated that exosomes can be isolated from natural milk, from both the skim milk fraction or the fat milk fraction, and that the isolated exosomes carry or encapsulate natural miRNA molecules, including miR-148 and miRNA-320, as well as anti-inflammatory proteins, such as TGF-β1.

Example 2

Exosomes Accumulated in the Intestine

To determine if milk derived exosomes can be taken up by the intestine, the following experiment was performed.

Figure 4A:
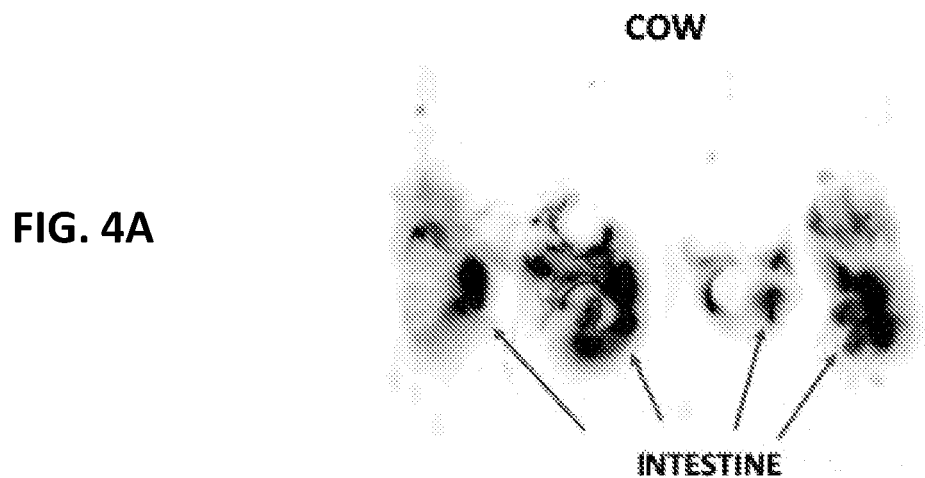
FIGS. 4A-C show that milk derived exosomes are taken up by the intestine of mice following oral administration.
Figure 4B:
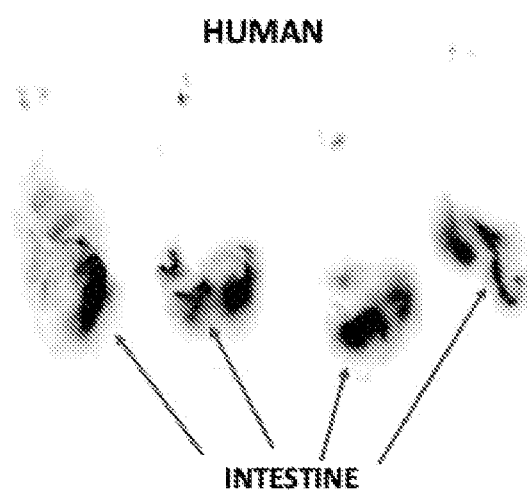
Figure 4C:
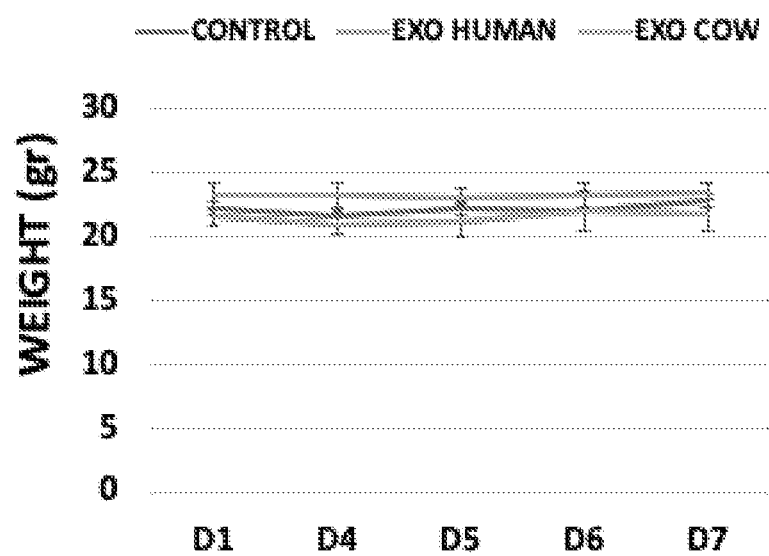

Milk derived exosomes (MDE) isolated from cow or human milk according to the protocols described above were gavage administered for 7 days to Balb/c mice (n=4/group) at a dose of 0.5 mg/ml per mouse in 200 μl PBS. MDE were labeled with an infrared fluorescent membrane dye, DiIR (Molecular Probes) according to the manufacturer's instructions to track exosome localization patterns in vivo. From day 6 to day 7, the DiR dye-labeled exosomes were administered by gavage to Balb/c mice. Two hours after gavage administration, mice were observed and fluorescence images for exosomes distribution were acquired with 740 nm excitation and 790 nm emission filters using Typhoon FLA 9500 scanner. Imaging revealed an accumulation of fluorescent signal in the intestine following gavage administration of cow or human milk derived exosomes (FIGS. 4A and 4B, respectively). Mice were weighted during the exosomes administration and the results presented in FIG. 4C showed that there was no effect of the exosomes on the body weight of the treated mice.

Thus, these results indicated that orally administered milk derived exosomes accumulated in the intestine.

Example 3

Orally Administered Milk Derived Exosomes Attenuated the Development of Colitis

To determine the preventive effect of milk derived exosomes on colitis, the animal model of dextran-sulfate sodium (DSS)-induced colitis in mice was used.

Colitis was induced in Balb/c mice by adding 5% DSS into the drinking water from day 1. Control mice received regular drinking water. Mice treated with DSS or control mice were either treated for 7 days with human milk derived exosomes (EXO) at a dose of 0.5 mg/ml per mouse in 200 µl PBS by gavage (DSS+EXO and EXO, respectively) or administered PBS only.

Figure 5A:
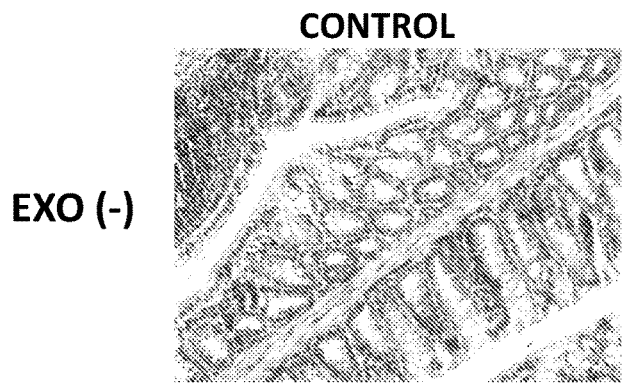
FIGS. 5A-F show that oral administration of milk derived exosomes prevented the development of colitis in a DSS mice model.
Figure 5B:
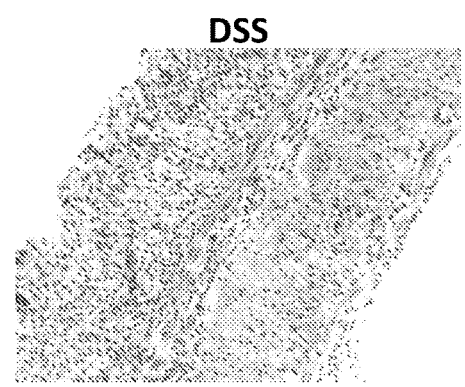
Figure 5C:
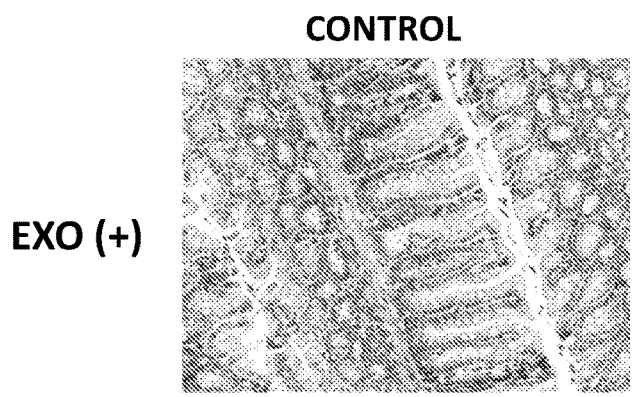
Figure 5D:
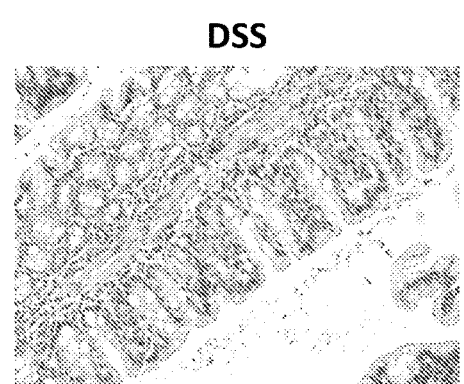
Figure 5E:
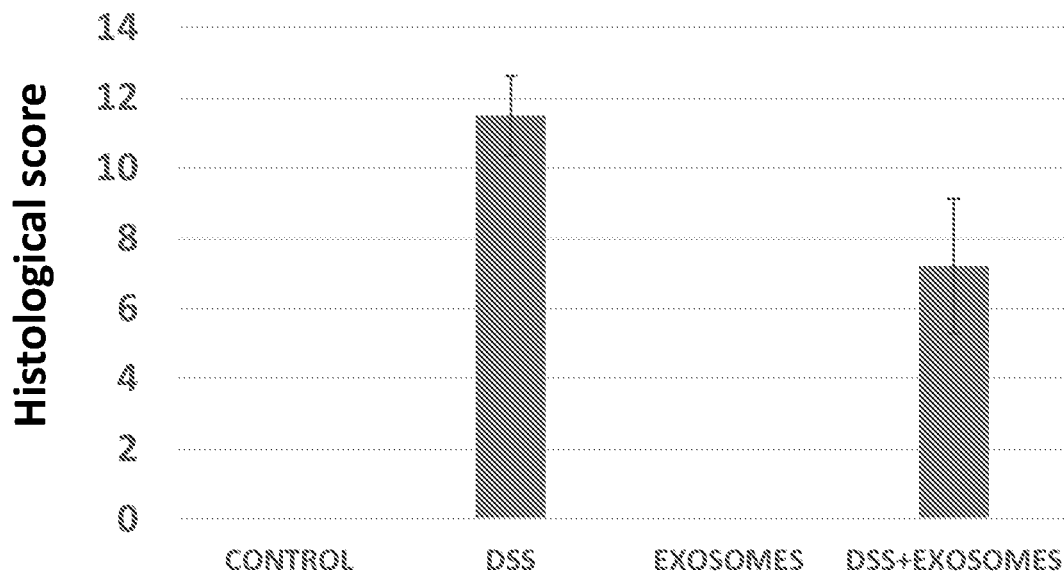
Figure 5F:
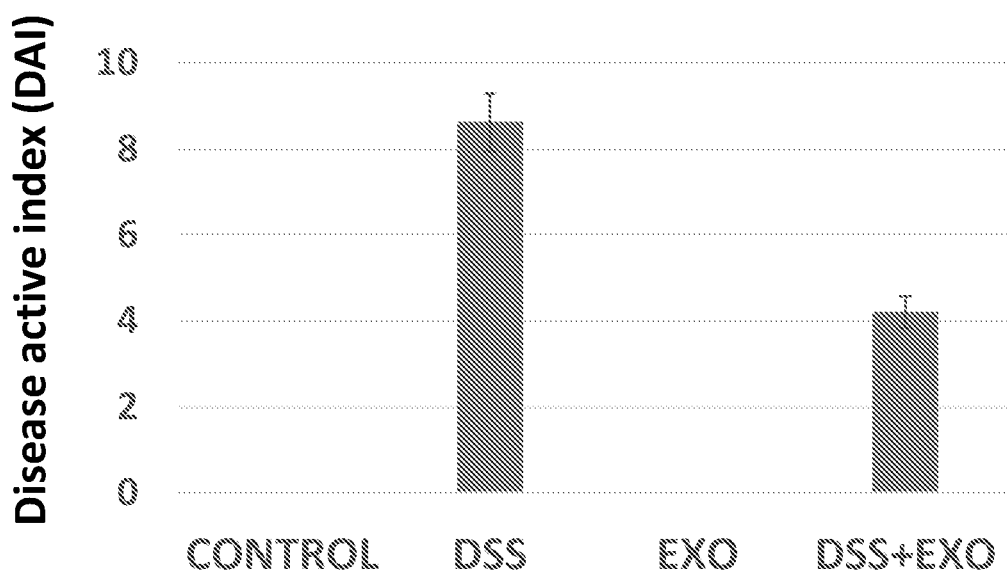

Representative colon sections from treated or control mice were stained by H&E, and the stained sections are shown in FIGS. 5A-D. Histological score of H&E stained sections is shown in FIG. 5E. FIG. 5F illustrates the disease activity index (which is the combined score of stool consistency, rectal irritation and blood in the stool, (DAI)) in the various tested groups (n=5/group).

The results of this experiment showed that the milk derived exosomes prevented the cellular damage in the colon of DSS-induced colitic mice (FIGS. 5D and 5E) as well as inhibited the development of colitis symptoms in these mice. Thus, MDE were shown to exert a beneficial effect in preventing or attenuating the development of DSS-induced colitis.

Example 4

Oral Administration of Milk Derived Exosomes Isolated from Cow or Human Milk Attenuated the Severity of Colitis Induced by DSS Next, the effect of MDE on colitic mice was evaluated.

Figure 6A:
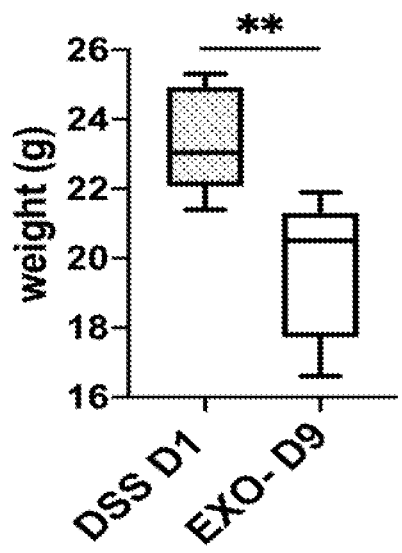
FIGS. 6A-H show that oral administration of milk derived exosomes isolated from cow or human milk attenuated the severity of DSS-induced colitis.
Figure 6B:
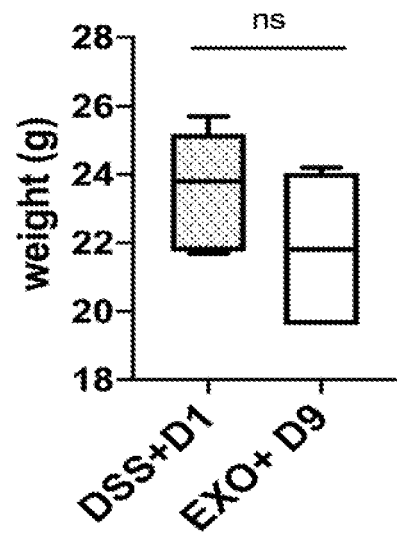
Figure 6C:
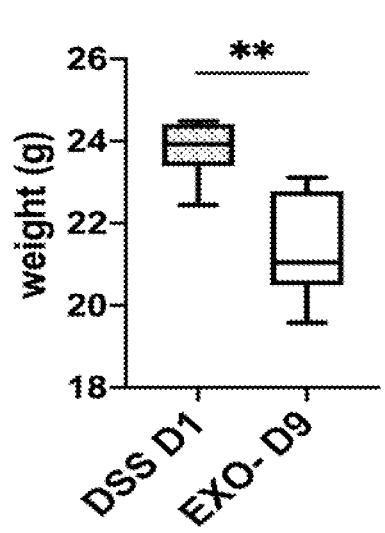
Figure 6D:
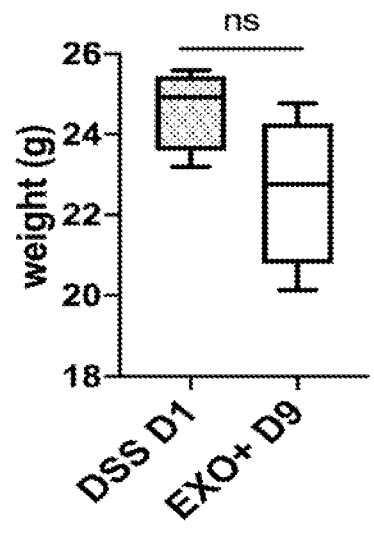

Colitis was induced in Balb/c mice using 5% DSS provided for one week in the drinking water. The mice were then treated for 5-6 days with exosomes (EXO+) or without exosomes (EXO-), as a control. During the seven days of DSS treatment and the two days of exosomes administration the weight of the mice was evaluated. As shown in FIGS. 6A and 6C, the weight of the mice decreased significantly during the seven days of DSS treatment and the two days without exosomes administration. However, administration of MDE isolated from cow or human milk for two days increased the mice' weight (FIGS. 6B and 6D, respectively) such that insignificant differences of the weight were seen compared to the initial mice' weight (FIGS. 6B and 6D). These results indicated that exosomes isolated from cow or human milk prevented weight loss associated with colitis and accelerated weight recovery.

Figure 6E:
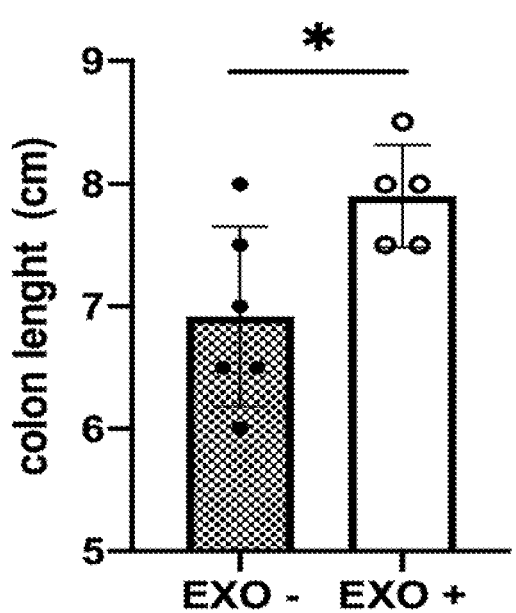
Figure 6F:
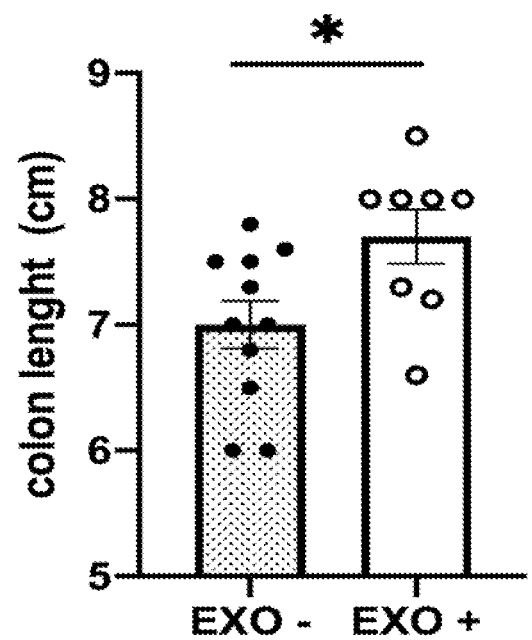
Figure 6G:
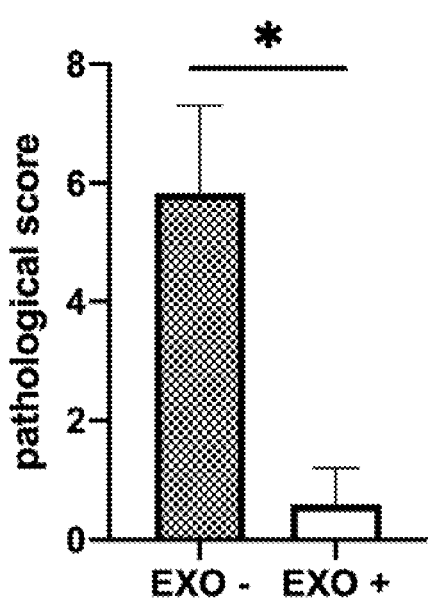
Figure 6H:
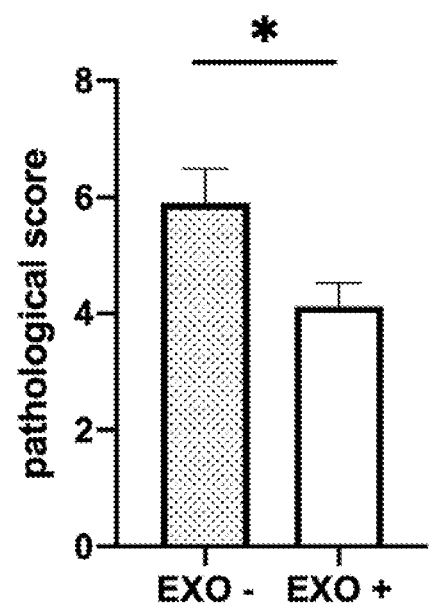

The exosomes isolated from cow or human milk diminished other signs and symptoms of DSS-induced colitis. Thus, the exosomes treatment significantly reduced the shortening of the colon: following cow milk derived exosomes treatment, the median length of the colon was 7.5 cm compared to 6 cm in the control group (FIG. 6E). Following human milk derived exosomes treatment, the median length of the colon was 7.7 cm compared to 7 cm in the control group (FIG. 6F). In addition, histological analysis of colon sections in untreated colitic mice revealed extensive colonic damage and immune cell infiltration (in the lamina propria and the mucosa), as compared to MDE treated colitic mice. This effect was reflected by the histological score: the exosomes isolated from cow milk reduced the histological score from 5.83 to 0.6 (FIG. 6G), and the exosomes isolated from human milk reduced the histological score from 5.9 to 4.13 (FIG. 6H).

Thus, these results indicated that MDE reduced the manifestations of DSS-induced colitis and attenuated its severity.

Example 5

MDEs Increased the Level of TGF-β1 in Colitic Colon

Figure 7A:
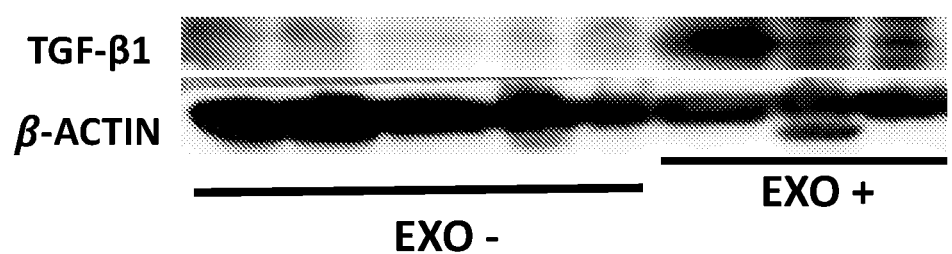
FIGS. 7A-B show the expression of TGF-β1 in colitic colon following MDE treatment.
Figure 7B:
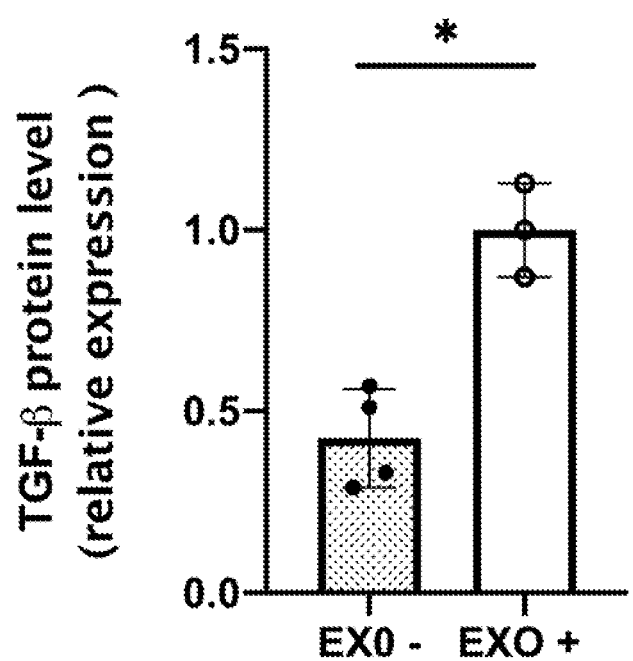

The next aim was to determine the effect of MDE treatment on the level of TGF-β1 protein in colitic colon. As shown in FIGS. 7A-B, following MDE treatment, there was a significant increase in TGF-β1 protein level in the colon tissue of colitic mice treated with MDE as compared to non-treated colitic mice. The protein level of β-actin, used as a control, was identical in MDE treated vs. non-treated colitic mice.

These results demonstrated that MDE treatment in colitic mice increased TGF-β1 expression in the colon.

Example 6

Effect of MDE on miRNAs Expression in Colitic Colon

Figure 8A:
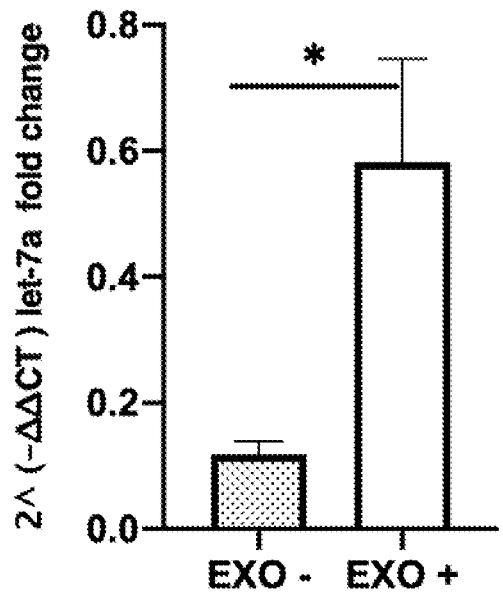
FIGS. 8A-D show the expression of milk highly expressed miRNA in colitic colon mice following MDE treatment. The expression of let7a (FIG. 8A), miRNA-320 (FIG. 8B), miRNA-375 (FIG. 8C) and miRNA-148 (FIG. 8D) in the colon of colitic mice which were treated with milk derived exosomes (EXO+) or not treated with exosomes (EXO−) is presented.
Figure 8B:
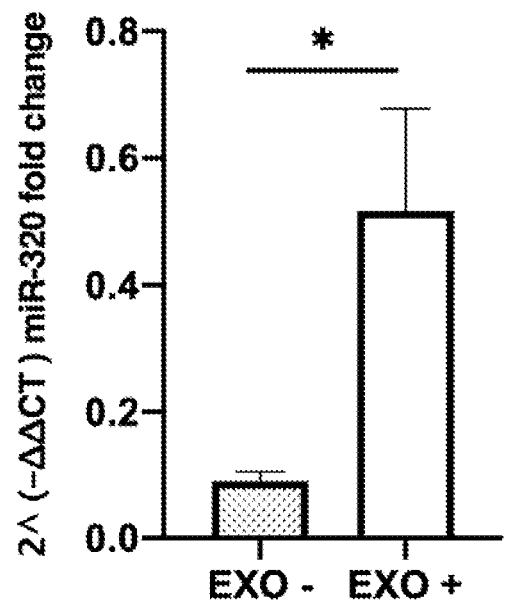
Figure 8C:
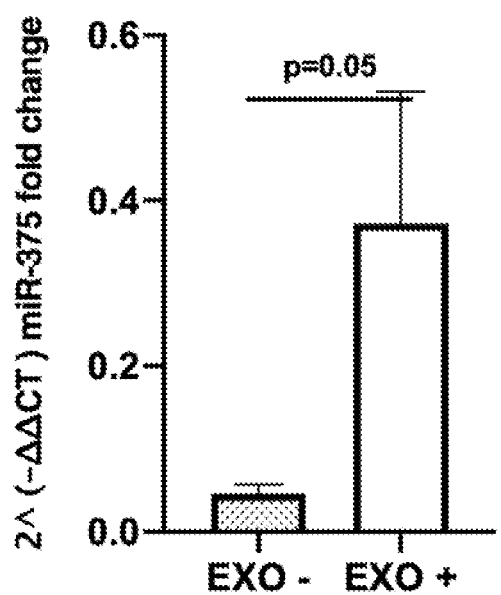
Figure 8D:
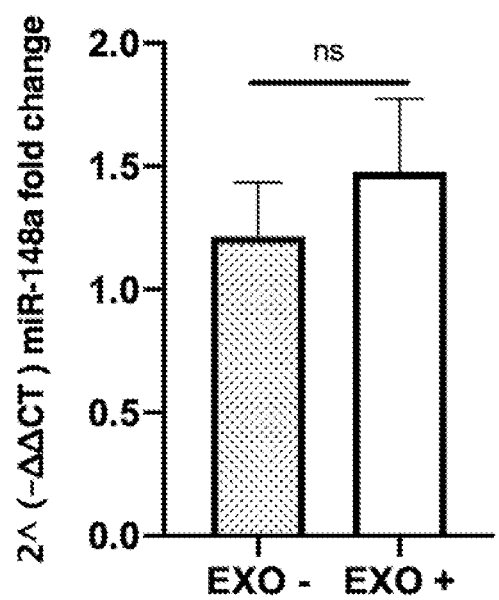

The effect of MDE treatment on miRNA expression in colitic colon of mice was next examined. Four miRNAs were analyzed in this study: miRNA-320, miRNA-375, let-7a, and miRNA148. These miRNAs along with additional eight miRNAs were found to be highly expressed in MDE (see WO 2017/090049). As shown in FIGS. 8A-D, the expression of let7a, miRNA-320, and miRNA-375 were significantly higher in MDE treated mice compared to untreated mice (FIGS. 8A, 8B and 8C, respectively). The expression of miRNA-148 was also higher in MDE treated mice compared to untreated mice (FIG. 8D).

These results showed that administration of MDE to colitic mice resulted in high expression of miRNAs in the colitic colon of the treated mice, implying that MDE affected miRNA expression in colitic colon.

Example 7

MDEs Affected Inflammation Elated Genes

Next, the effect of MDE on the expression of pro-inflammatory cytokines in colitic colon was evaluated.

Figure 9A:
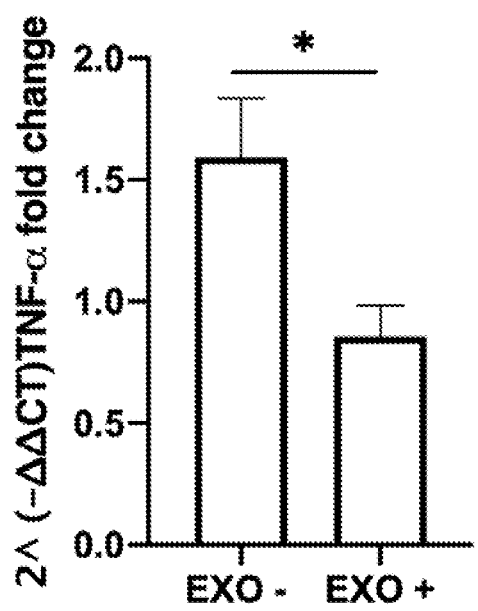
FIGS. 9A-B show the expression of IL-6 and TNF-α genes in the colon of colitis mice following MDE treatment. Gene expression of TNF-α (FIG. 9A) or IL-6 (FIG. 9B) was determined in the colon of colitic mice treated with exosomes (EXO+) or not treated with exosomes (EXO−).
Figure 9B:
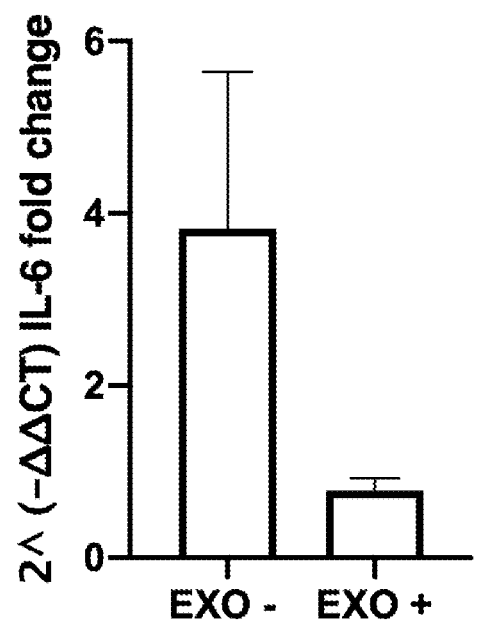

As shown in FIGS. 9A-B, lower gene expression of the pro-inflammatory cytokines: TNF-α and IL-6, was observed in the MDE treated colitic mice compared to the non-treated collie mice. The expression of TNF-α gene was significantly down regulated following MDE treatment (FIG. 9A). In addition, gene expression of IL-6 was down regulated in the MDE treated mice compared to the non-treated (FIG. 9B).

Taken together, these results showed that MDE treatment not only did it increased the expression of the anti-inflammatory cytokine TGF-β1 in colitic colon of mice, but also reduced the expression of the pro-inflammatory cytokines: IL-6 and TNF-α in this tissue. Milk derived exosomes are therefore a useful medication for treating and/or preventing colitis.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

What is claimed is:

1. A method of treating an inflammatory bowel disease (IBD) comprising administering to a subject in need of such treatment a composition comprising a therapeutically effective amount of exosomes isolated from milk by centrifugation and filtration but without any structural modification after isolation, wherein the exosomes comprise one or more miRNA molecules, and TGF-β, wherein the composition is administered by enteral route of administration, thereby treating the IBD.

2. The method according to claim 1, wherein the milk is bovine, goat, or human milk.

3. The method according to claim 1, wherein the exosomes are isolated from a skim fraction of the milk and/or from a fat fraction of the milk.

4. The method according to claim 1, wherein the one or more miRNA molecules are selected from the group consisting of let-7a, miR-320, miR-375, and miR-148a.

5. The method according to claim 1, wherein the TGF-β is TGF-β1.

6. The method according to claim 1, wherein the exosomes further comprise at least one biologically active compound selected from the group consisting of proteins, peptides, nucleic acid molecules, and lipids.

7. The method according to claim 1, wherein the exosomes comprise less than about 20% (w/w) casein of the total protein of the exosomes.

8. A method of treating an inflammatory bowel disease (IBD) selected from the group consisting of Crohn's disease and ulcerative colitis, comprising administering to a subject in need of such treatment a composition comprising a therapeutically effective amount of exosomes isolated from milk by centrifugation and filtration but without any structural modification after isolation, wherein the exosomes comprise one or more miRNA molecules, and TGF-β, wherein the composition is administered by enteral route of administration, thereby treating the IBD.

9. The method according to claim 8, wherein ulcerative colitis is distal colitis.

10. The method according to claim 9, wherein distal colitis is selected from the group consisting of proctitis, proctosigmoiditis, and left-sided colitis.

11. The method according to claim 1, wherein the composition is administered by oral administration or by tube feeding.

12. The method according to claim 1 wherein the composition is administered by rectal administration.

13. The method according to claim 12, wherein the composition is formulated as an enema, suppository, or foam.

14. The method according to claim 1, wherein the therapeutically effective amount of the exosomes ranges from about 0.1 mg to about 250 mg/kg body weight of the subject.

15. The method according to claim 13, wherein the milk in the composition is bovine, goat, or human natural milk.

16. The method according to claim 15, wherein the one or more miRNA molecules are selected from the group consisting of let-7a, miR-320, miR-375, and miR-148a.

17. The method according to claim 15, wherein the exosomes further comprise at least one biologically active compound selected from the group consisting of proteins, peptides, nucleic acid molecules, and lipids.

18. A method of treating an inflammatory bowel disease (IBD) comprising administering to a subject in need of such treatment a composition comprising a therapeutically effective amount of exosomes isolated from bovine, goat, or human milk by centrifugation and filtration but without any structural modification after isolation, wherein the exosomes comprise one or more miRNA molecules selected from the group consisting of let-7a, miR-320, miR-375, and miR-148a and comprise less than about 20% (w/w) casein of the total protein of the exosomes, with the composition further comprising TGF-β1 and at least one biologically active compound selected from the group consisting of proteins, peptides, nucleic acid molecules, and lipids, wherein the composition is administered by enteral route of administration and the therapeutically effective amount of the exosomes ranges from about 0.1 mg to about 250 mg/kg body weight of the subject, thereby treating the IBD.

* * * * *